(12) United States Patent
Ohmiya et al.

(10) Patent No.: US 8,383,797 B2
(45) Date of Patent: Feb. 26, 2013

(54) LUCIFERASE GENE OPTIMIZED FOR USE IN IMAGING OF INTRACELLULAR LUMINESCENCE

(75) Inventors: Yoshihiro Ohmiya, Ikeda (JP); Yoshihiro Nakajima, Ikeda (JP); Vadim Viviani, Ikeda (JP); Shigeaki Nishii, Tsuruga (JP); Tomomi Asai, Tsuruga (JP)

(73) Assignees: Toyo Boseki Kabushiki Kaisha, Osaka-shi, Osaka (JP); National Institute of Advanced Industrial Science and Technology, Tokyo (JP)

( * ) Notice: Subject to any disclaimer, the term of this patent is extended or adjusted under 35 U.S.C. 154(b) by 1107 days.

(21) Appl. No.: 12/093,901

(22) PCT Filed: Nov. 13, 2006

(86) PCT No.: PCT/JP2006/322548
§ 371 (c)(1),
(2), (4) Date: Aug. 8, 2008

(87) PCT Pub. No.: WO2007/058140
PCT Pub. Date: May 24, 2007

(65) Prior Publication Data
US 2009/0220960 A1 Sep. 3, 2009
US 2010/0112553 A2 May 6, 2010

(30) Foreign Application Priority Data

Nov. 16, 2005 (JP) .................................. 2005-332007

(51) Int. Cl.
*C07H 21/04* (2006.01)
*C12N 15/85* (2006.01)
(52) U.S. Cl. ....................... 536/23.2; 536/23.4; 435/325
(58) Field of Classification Search ........................ None
See application file for complete search history.

(56) References Cited

U.S. PATENT DOCUMENTS

| 5,670,356 A | 9/1997 | Sherf et al. |
| 2007/0105172 A1 | 5/2007 | Ohmiya et al. |

FOREIGN PATENT DOCUMENTS

| EP | 1 621 634 A1 | 2/2006 |
| WO | WO 02/16944 A2 | 2/2002 |
| WO | WO 2004/025264 A2 | 3/2004 |
| WO | WO 2004/099421 A1 | 11/2004 |
| WO | WO 2005/015161 A2 | 2/2005 |
| WO | WO 2005/038029 A2 | 4/2005 |
| WO | WO 2007/027919 A2 | 3/2007 |

OTHER PUBLICATIONS

Loetscher et al. The C terminus of mouse ornithine decarboxylase confers rapid degradation on dihydrofolate reductase. Support for the pest hypothesis. J Biol Chem. Jun. 15, 1991;266(17):11213-20.*
Zanta et al. Gene delivery: a single nuclear localization signal peptide is sufficient to carry DNA to the cell nucleus. Proc Natl Acad Sci U S A. Jan. 5, 1999;96(1):91-6.*
Hirokawa et al., *Biochimica et Biophysica Acta*, 1597: 271-279 (2002).
Kitayama et al., *Photochemistry and Photobiology*, 77(3): 333-338 (2003).
Viviani et al., *Photochemistry and Photobiology*, 70(2): 254-260 (1999).
Baggett et al., *Molecular Imaging*, 3(4): 324-332 (Oct. 2004).
Ozawa et al., *Anal. Chem.*, 73: 2516-2521 (2001).
Sala-Newby et al., *Immunology*, 93: 601-609 (1998).
Viviani et al., *Photochemistry and Photobiology*, 76(5): 538-544 (2002).
Nakajima et al., *Biotechnology Journal*, 5(4): 453-455 (Jul. 2005).
Ohmiya et al., *Upload*, 79: 1-2 (2005).

* cited by examiner

*Primary Examiner* — Michele K Joike
(74) *Attorney, Agent, or Firm* — Leydig, Voit & Mayer, Ltd.

(57) ABSTRACT

The present invention provides a gene construct encoding pH insensitive luciferase for visualizing intracellular information, wherein an intracellular expression activity is higher compared with a gene construct of luciferase derived from a firefly.

20 Claims, 12 Drawing Sheets (A)

(B)

LUCIFERASE GENE OPTIMIZED FOR USE IN IMAGING OF INTRACELLULAR LUMINESCENCE

INCORPORATION-BY-REFERENCE OF MATERIAL ELECTRONICALLY

SUBMITTED

Incorporated by reference in its entirety herein is a computer-readable nucleotide/amino acid sequence listing submitted herewith and identified as follows: 8,837 bytes ASCII (Text) file named "703019ReplacementSequenceListing-3rd.txt," created Apr. 11, 2012.

TECHNICAL FIELD

The present invention relates to a gene construct of luciferase wherein a luminescence intensity in living cells is enhanced for the purpose of cell imaging, a combination thereof, a cell transformed with the gene construct, and a method for evaluating an interaction of two proteins in a cell.

Furthermore, the present invention relates to a highly sensitive method for monitoring transcription activity in living cells using a gene construct of luciferase whose expression is enhanced, and more particularly relates to a method for a high-throughput analysis using a plate format.

BACKGROUND ART

In the field of life science, it is very important to analyze various phenomena that occur in cells, e.g., to monitor changes of intracellular calcium ion concentration, phosphorylation of intracellular proteins, distributions of ATP, which is an energy, or transcription activities of the genes. In order to analyze them, various molecular probes have been developed and applied for imaging. In particular, various fluorescent proteins are used as tools for cell imaging. Fluorescent protein fluoresces without a cofactor immediately after being expressed in a cell. The fluorescent protein is utilized as a monitor protein for localization of the protein in a cell, using fluorescence as an indicator. However, quantification is difficult because of the requirement of an excitation light and uneven fluorescence efficiency, and the cells are impaired because of exposure to the excitation light. Thus, fluorescent protein is not suitable for long-term observation.

The measurement of the transcription activity using a reporter gene is the tool used to analyze various intracellular molecular mechanisms, e.g., the analysis of the activation of intracellular signal transduction or the analysis of receptor-ligand interaction by measuring an expressed amount of the reporter gene linked to a certain promoter, in addition to the analysis of a gene expression regulatory sequence such as a promoter, an enhancer and a silencer or a transcription factor bound thereto. This technique is used as a large-scale screening tool in drug discovery and toxicity evaluation of chemicals.

The reporters used here include many enzymes such as chloramphenicol acetyl transferase (CAT), β-galactosidase, and green fluorescent protein (GFP). A system using the bioluminescence of firefly luciferase is widely used currently because it is highly sensitive and simpler to be assayed than other reporter enzyme. GFP does not require a substrate and can be easily detected by irradiating the excitation light, but is not suitable for quantification. Since the excitation light is irradiated, the cells are greatly damaged. Thus, GFP is not suitable for long-term, continuous monitoring purposes.

Firefly luciferase is luciferase derived from luminescent beetles, and cDNA thereof has been isolated from the fireflies belonging to genera *Photinus, Photuris* and *Luciola*. In particular, the gene derived from *Photinus pyralis* has been studied in detail over the years. Luciferases derived from beetles including the firefly act on a poly-heterocyclic organic acid, D-(−)-2-(6'-hydroxy-2'-benzothiazolyl-Δ2-thiazoline-4-carboxylic acid (hereinafter represented as luciferin) as a substrate, and catalyze a reaction of ATP and luciferin in the presence of Mg ion to form luciferyl adenylate, which is bound to oxygen to generate oxyluciferin in an excited state. Luminescence is emitted when this oxyluciferin relaxes to a ground state.

Firefly luciferase is used as the reporter gene for the evaluation of effects of exogenous factors on the cells, propagation of the intracellular signal transduction or expression of individual proteins. A system is included in which the amount of luciferase synthesized intracellularly is measured to evaluate transcriptional activity by linking a transcriptional regulatory region to a firefly luciferase gene, introducing the gene construct into cells, treating the cultured cells transfected with the reporter gene with a drug for a certain time period, and subsequently collecting the cells and adding a luminescent substrate. The system has excellent quantitative properties because transcriptional activity is evaluated with the luminescence amount of luciferase, and products related to this system have been developed and made commercially available from many companies.

As the imaging using firefly luciferase, for example, the change of an ATP in the cells has been successfully visualized by measuring the ATP amount using firefly luciferase, in which the change of the intercellular calcium concentration being visualized using a photoprotein, Aequorin (Non-Patent Literature 1). Another example discloses an intermolecular force between the proteins successfully visualized by a firefly luciferase split assay (Non-Patent Literature 2). Although luciferase imaging is not as suitable as fluorescent proteins for analysis at molecular level and for microscopic imaging inside a cell, it enables the obtainment of cellular information that cannot be measured using fluorescent protein in the analysis of the phenomena that occur in the cells at an organelle level, and particularly in long-term measurement. Firefly luciferase imaging is an effective method for the evaluation and screening of pharmaceuticals.

However, there are few examples of firefly luciferase imaging. This is because the stability of luciferase in mammalian cells is lower, the protein lifespan is shorter compared with the fluorescent protein, and the transcription efficiency is low; firefly luciferase is thus not suitable for practical use, as image analyzers of the cells correspond to the fluorescence, and no imaging system for efficiently measuring the luminescence is available. This is particularly because the luminescence intensity of firefly luciferase in living cells is low, thus hindering the easy obtainment of luminescence signals.

Among firefly luciferases, the enzyme used most frequently for imaging and the like is luciferase derived from fireflies produced in North America (*Photinus pyralis*). It has been reported recently that the mutants having improved thermal stability and their half-lives prolonged by about 2 to 25 times in vitro emits enhanced luminescence signal in the cells and are suitable for cell imaging (Non-Patent Literature 3). However, one shortcoming of firefly luciferase is that the luminescent color is changed in conjunction with the intracellular pH value, and thus is not suitable for analyzing multiple gene expressions based on the diversity of luminescent colors (Yoshihiro Ohmiya, Yoshihiro Nakajima, Multiple Gene Transcription Activity Measurement System; Patent Document 1).

Luciferase expressed in an animal or a cell in which a beetle-derived luciferase gene has been introduced can be detected with its luminescence by administering luciferin into the animal, or by adding luciferin to the cell culture and permeating it into the cell to perform a luciferase-luciferin reaction.

However, in many cases, luciferase expressed in the cell is detected by lysing the cell with a reagent containing a surfactant, mixing the luciferase-containing cell lysate with the luminescent substrate reagent and measuring the luminescence of luciferin. This method is complicated because the cell is lysed and luciferase further reacted with the luminescent reagent, compared with the method of detection adding luciferin to the cell culture medium. Once the cell is lysed, further phenomenon in the cell cannot be observed. Meanwhile, one merit of the method above, in which the cell is not lysed, is that the intracellular phenomenon can be continuously observed by prolonging a culture time period as needed. Despite its drawbacks, the cell-lysing detection method is currently mainstream. The major reasons for this are that the firefly luciferase reporter does not react sufficiently with luciferin in the living cells, the signals are weak and the sensitivity is low. These shortcomings become remarkable when a promoter having weak transcription activity is analyzed or a transient assay of the reporter gene is performed using cells having a low gene introduction efficiency. Additionally, when multiple samples are measured simultaneously, the sample amount is reduced and measurement is difficult in a detection system with low sensitivity. Thus, a reporter assay method in which the transcriptional activity can be monitored efficiently in living cells has been required.

Patent Document 1: WO2004/99421
Non-Patent Literature 1: Sala-Newby G B et al.: Imaging bioluminescent indicators shows Ca2+ and ATP permeability thresholds in live cells attacked by complement. Immunology. 1998 April; 93 (4):601-9
Non-Patent Literature 2: Ozawa T. et al.: Split luciferase as an optical probe for detecting protein-protein interactions in mammalian cells based on protein splicing. Anal. Chem., 2001 Jun. 1; 73 (11):2516-21
Non-Patent Literature 3: Baggett B. et al., Thermostability of firefly luciferases affects efficiency of detection by in vivo bioluminescence. Mol. Imaging, 2004 October; 3 (4):324-32.

It is important when developing or evaluating a drug, or when evaluating the toxicity of chemicals, to evaluate the effects of a exogenous factor on a living body. Evaluation using organism individuals such as mice and evaluation using tissues and cell populations have advanced, and further, intercellular and intracellular information changes are currently examined at single cell level to evaluate the exogenous factor. Thus, a molecular probe for evaluating the intercellular and intracellular information change becomes important for evaluating the exogenous factor. The fluorescent protein is suitable as an intracellular imaging probe for short-term measurement, but is not suitable for long-term analysis. Luciferase is suitable for long-term measurement, but has not been established as an imaging tool.

To establish luciferase as an intracellular and intercellular imaging tools, high stability and a relatively long protein lifespan of luciferase in the mammalian cell are desired. It is also desired that luciferase fused with various tag protein domains have high luminescence intensity. The sufficient luminescence intensity and stability were not found in luciferase derived from the fireflies produced in North America and Japan conventionally used for measuring the transcriptional activity in the mammalian cells. In particular, stable measurements are difficult in luciferases derived from fireflies produced in North America and Japan because the luminescence spectra changes depending on environmental pH values.

DISCLOSURE OF INVENTION

Problem to be Solved by the Invention

It is an object of the present invention to provide a gene construct that is insensitive to intracellular pH values and enables imaging in an individual cell for a long term causing little to no cellular damage, and a transformed cell, particularly a transformed human cell.

It is another object of the present invention to provide a method of dividing luciferase to introduce as fusion proteins into a cell and imaging an interaction between respective proteins fused with respective portions of luciferase, a transformed cell capable of undergoing the imaging, and a combination of gene constructs encoding such fusion proteins.

It is still another object of the present invention to provide a highly sensitive method to measure transcriptional activity in living cells. More particularly, the present invention provides a method to measure transcriptional activity using living cells effective for analysis of a promoter having low transcriptional activity, transient assay in the cells having low gene introduction efficiency, and assay in plate format, which has small volume of sample.

Means for Solving the Problem

As a result of an extensive study in the light of the above problems, the present inventor has found that luciferase derived from a click beetle (*Pyrearinus termitilluminans*) produced in Brazil has high stability and a long lifespan property in the mammalian cell, and particularly enables luminescence imaging in the mammalian cell.

The present inventor further applied click beetle-derived luciferase exhibiting high activity in living cells such as a mammalian cells to the measurement of transcriptional activity, and found it was possible to measure the activity stably and with high sensitivity in the promoter having weak transcription activity, or in the cell having low gene introduction efficiency compared with assays using conventional firefly luciferase, and completed the present invention.

The present invention provides the following gene construct, transformed cell, method for analyzing an interaction between heteroproteins in the cell, and method for measuring the transcriptional activity.

(1) A gene construct encoding pH-insensitive luciferase, wherein an intracellular expression activity is higher than that of a gene construct of luciferases derived from fireflies.

(2) The gene construct according to (1), wherein the cell is a mammalian cell.

(3) The gene construct according to (2), wherein the gene construct is comprised of a luciferase gene having effective translation in the mammalian cell.

(4) The gene construct according to any of (1) to (3), wherein the gene construct encodes click beetle-derived luciferase.

(5) The gene construct according to (4), wherein click beetle-derived luciferase is selected from the group consisting of luciferases belonging to genus *Pyrophorus* or *Pyrearinus* or mutants thereof.

(6) The gene construct according to (4) or (5), wherein a gene encoding click beetle-derived luciferase has a base sequence of SEQ ID NO: 2.

(7) The gene construct according to any of (1) to (6), wherein pH-insensitive luciferase is destabilized luciferase.

(8) The gene construct according to any of (1) to (7), wherein the gene construct encodes a fusion protein comprised of a pH-insensitive luciferase sequence or a partial sequence thereof and at least one heteroprotein sequence or tag sequence.

(9) The gene construct according to (8), wherein the heteroprotein sequence or tag sequence is a protein destabilizing signal.

(10) The gene construct according to (9), wherein the protein destabilizing signal has a PEST sequence.

(11) The gene construct according to (10), wherein the PEST sequence is a 3'-terminus of murine ornithine decarboxylase or a mutant thereof.

(12) The gene construct according to (8), wherein the heteroprotein sequence of tag sequence is an intracellular localization signal.

(13) The gene construct according to (8) encoding a fusion protein comprised of an N terminal region of the pH-insensitive luciferase and at least one first heteroprotein.

(14) The gene construct according to (8) encoding a fusion protein comprised of a C terminal region of the pH-insensitive luciferase and at least one second heteroprotein.

(15) A combination of the gene construct of (13) and the gene construct of (14).

(16) A method for evaluating an interaction between the first heteroprotein and the second heteroprotein by introducing the gene constructs encoding the fusion proteins of (13) and (14) into a same cell to express the fusion proteins.

(17) A method for evaluating an interaction between the first heteroprotein and the second heteroprotein by mixing expression products from the gene constructs according to (13) and (14).

(18) A transformant cell transformed using the gene construct of (1) to (14) or the combination of the gene constructs according to (15).

(19) The transformant cell according to (18), wherein the cell is a mammalian cell.

(20) The transformant cell according to (18) or (19) wherein the cell is a human cell.

(21) A modified gene of a luciferase gene derived from a click beetle according to SEQ ID NO: 2.

(22) Use of the transformant cell according to any of (18) to (20) for imaging of an intracellular organelle.

(23) A method for measuring a transcription activity comprising culturing a test cell which expresses pH-insensitive luciferase under control of a transcription control sequence subjected to a test under a desired condition and measuring a luminescence by the expressed luciferase in a living cell, wherein an intracellular expression activity of the pH-insensitive luciferase is higher than that of luciferase derived from a firefly.

(24) The method according to (23), wherein the pH-insensitive luciferase is click beetle-derived luciferase.

(25) The method according to (23) or (24), wherein the pH-insensitive luciferase is selected from the group consisting of luciferases derived from the click beetle belonging to genus *Pyrophorus* or *Pyrearinus*, or mutants thereof.

(26) The method according to any of (23) to (25), wherein a pH-insensitive luciferase gene under the control of the transcription control sequence has a base sequence represented by SEQ ID NO: 2.

(27) The method according to any of (23) to (26), wherein the pH-insensitive luciferase is destabilized.

(28) The method according to any of (23) to (27), wherein the cell is selected from the group consisting of mammalian cells, yeast, *Escherichia coli* and plant cells.

(29) The method according to any of (23) to (28), wherein the transcription control sequence to be tested is a sequence having a low transcription activity.

(30) The method according to any of (23) to (29), wherein the cell is a cell having a low gene introduction efficiency.

(31) The method according to any of (23) to (30), wherein 0.01 to 10 mM D-luciferin is added to a cell culture medium.

(32) The method according to any of (23) to (31), which is performed in a 96-, 384- or 1,536-well plate format.

(33) The method according to any of (23) to (32), wherein an effect of a compound on the cell is evaluated by expression difference of luciferase.

EFFECT OF THE INVENTION

According to the present invention, the intracellular amount of expressed luciferase can be widely enhanced, and it has become possible to perform bioluminescence imaging in an individual cell for a long term. In a system using luciferase, it is not necessary to consider cell damage due to the short term cell imaging exposed to the excitation light, long-term cell imaging becomes possible, and the system can be utilized for the treatment of various pathological conditions and drug discoveries.

According to the method of the present invention, particularly in the analysis of the promoter having weak transcription activity and the analysis of the promoter in the cell having low gene introduction efficiency, the sensitivity is improved and stable measurement becomes possible compared with those using conventional firefly luciferase. Furthermore, by enhancing the signal intensity according to the method of the present invention, it becomes possible to analyze living cells in the plate format, in the test in which it was difficult to treat multi-samples in the plate format due to the small amount of the samples. Thus, an application range to analyze living cells can be expanded in drug discovery screenings and cytotoxic evaluations of chemicals.

BRIEF DESCRIPTION OF DRAWINGS

in FIG. 5, nuclear localization signal: DPKKKRKVDPKKKRKVDPKKKRKV (SEQ ID NO: 16), endoplasmic reticulum localization signal: MGWSCIILFLVATATGAHS—SEKDEL (SEQ ID NO: 17), and membrane localization signal: MLCCMRRT-KQVEKNDEDQKI (SEQ ID NO: 18);

in FIG. 6, (A) bioluminescence imaging, (B) anti-FLAG antibody, (C) GFP, (D) superposition, (E) peroxisome, (F) nucleus, (G) cytoplasm and (H) fluorescence imaging;

BEST MODES FOR CARRYING OUT THE INVENTION

Figure 5:
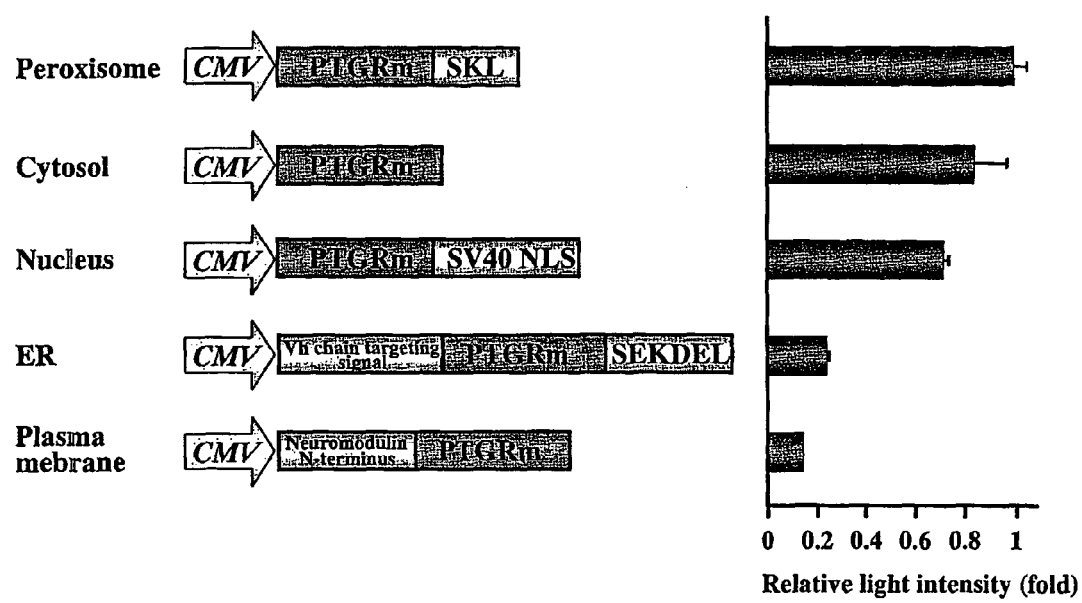
FIG. 5 is a view showing structures of mutants obtained by linking intracellular localization peptide sequences to the click beetle luciferase mutant type (PtGRm), and the luminescence intensity thereof.

The gene construct of the present invention when expressed in the cells (particularly the mammalian cells) has enhanced expression efficiency compared with the gene construct of conventional luciferase derived from the firefly (*Photinus Pyralis*), and enables imaging in each cell (see, e.g., FIG. 5).

In the transformed cell in which conventional firefly luciferase has been introduced, the bioluminescence signal is not significant; in the firefly luciferase mutant described in Non-Patent Document 3, the bioluminescence signal is still low and insufficient for bioluminescence imaging.

Meanwhile, the cell transformed with the gene construct of the present invention has a luminescence amount that is two times or more, preferably 4 times or more, more preferably 10 times or more, still more preferably 25 times or more and particularly 100 times or more larger than the cell transformed with the gene construct of luciferase derived from the firefly (*Photinus Pyralis*).

In one preferable embodiment of the present invention, the gene construct of the present invention can be an expression vector comprising multicloning sites for introducing a luciferase gene, the luciferase gene, a promoter and/or an enhancer (transcription control sequence) for regulating the expression of the gene, a polyadenylation sequence, a selectable marker gene and an origin of replication and the like. The transcriptional control sequence such as a promoter and enhancer is a target whose transcription regulation is measured by the luciferase of the present invention.

Luciferase encoded by the gene construct of the present invention is pH-insensitive, i.e., its luminescence wavelength does not change substantially depending on pH. The luciferase is not particularly limited as long as it has such a property, and luciferase derived from the click beetle is more preferably encoded by the gene construct of the present invention. As the luciferase gene derived from the click beetle, the gene of SEQ ID NO: 1 is exemplified. Click beetle-derived luciferase exhibits not only pH-insensitive luminescence wavelength but also significantly high stability (i.e., slow intracellular decomposition) compared with other luciferases, and thus is also preferable in these respects.

Since the luminescence wavelength in firefly luciferase changes depending on pH, the precise imaging is difficult in an intracellular environment where the pH value is always changed.

Both click beetle-derived luciferase and firefly luciferase have the maximum luminescence at pH 8.0, but the pH value in the cytoplasm is 7.2, which is slightly lower than the optimal pH of luciferase. In the detection of intracellularly expressed firefly luciferase conventionally performed generally, the cells are lysed and the reaction is performed in a buffer at around pH 8.0 whereas a reaction efficiency is poor in the living cells due to the low pH value. Meanwhile, click beetle-derived luciferase maintains the higher reaction efficiency at lower pH compared with firefly luciferase, and is suitable for the assay in the living cells. The click beetle-derived luciferase of the present invention can be sufficiently measured when the intracellular pH value is 6.5 or higher, and the intracellular pH value is preferably 7 or higher, more preferably 7.0 to 8.5 and particularly 7.4 to 8.0.

The high intracellular stability of click beetle-derived luciferase is effective for the analysis of the transcriptional control sequence having low expression activity, the analysis of the intracellular localization, the monitoring of the organelle in which luciferase has been localized, and the analysis of the function and the amount of the heteroprotein fused to luciferase. However, this stability makes monitoring the increase or decrease of change in transcriptional activity difficult in some cases. In this case, it is preferable to promote intracellular decomposition, and click beetle-derived luciferase, whose intracellular lifespan is shortened, keeps higher luminescence reaction efficiency, even at low pH, than firefly luciferase, and is useful as a luciferase having a short lifespan and a high signal intensity. Meanwhile generally, the amount of intracellular transcription products of a gene group such as housekeeping genes that are expressed in certain amounts in many tissues and cells and involved in maintenance and proliferation of the cells is large while the expression of the genes responsible for functional regulation of the cells is often low. Among cytokines encoded by such genes having low expression amounts, the expression of IL-6 is promoted in many tumors with inflammation, IL-6 is suggested to be involved in the progress of cancers, and it has been reported that an anti-IL-6 antibody has excellent therapeutic effects on multiple myeloma and plasma cell leukemia. Alternatively, the expression amounts of IL-8 and ICAM-1 that are cytokine/chemokine in bronchial pathway epithelial cells are promoted in non-smokers, healthy smokers and patients with chronic obstructive lung disease in this order. It is very useful for elucidation of disease mechanisms and drug discovery to screen the compounds that inhibit the promotion action of these diseases using an expression control region of such genes. By the use of luciferase having a higher detection capacity, it is possible to perform a cellular assay for the transcriptional control sequence of the gene that could not be sufficiently detected or quantified due to low transcriptional efficiency using conventional firefly luciferase. The transcriptional control sequence mentioned here further includes sequence regions referred to as the enhancer and the silencer, which are involved in the promotion or inhibition of the transcription along with the sequence region referred to as the promoter, which is required for transcriptional initiation. As a procedure to analyze regulation by the enhancer or the silencer, substituting the base sequence at the site supposed to be the site of the sequence to be tested with the other base sequence or removing the region by using a gene engineering technique, whether the regulation of the gene expression is maintained is evaluated. Alternatively, by ligating the sequence supposed to be the enhancer or the silencer to the promoter sequence known to be expressed at a certain level, whether the expression of luciferase is promoted or inhibited is evaluated.

A naturally occurring luciferase gene may itself be used as the luciferase gene used in the present invention; however, it is preferable to modify the gene sequence to make translational efficient in the cell in which the gene construct is introduced. Specifically, (a) a cDNA sequence can be changed so that an additional transcriptional factor is not bound, (b) a codon usage (frequency bias of codon usage) for insects can be changed to the codon usage for the desired cells (e.g., for mammals) in the cDNA sequence, and (c) the cDNA sequence can be changed because many restriction enzyme sites limit its practical application in use. By appropriately combining them to enhance translation efficiency, it is possible to increase the expression amount of luciferase and increase the luminescence amount to an extent that bioluminescence imaging can be easily performed. For example, a mutant of SEQ ID NO: 2 obtained by modifying the click beetle luciferase gene has a luminescence amount that is about 150 times larger than the gene of SEQ ID NO: 1 before the modification. Two methionine residues line side by side in an initiation codon and the second codon in SEQ ID NO: 1 whereas in SEQ ID NO: 2, one methionine residue is deleted but the luminescence was observed to be sufficiently amplified. Thus, the number of the methionine residues may be either one or two. The gene encoding pH-insensitive luciferase of the present invention includes a mutant gene that hybridizes with DNA of SEQ ID NO: 2 under a stringent condition and has a higher expression activity in the cell (particularly the mammalian cell) than the luciferase gene derived from *Photinus Pyralis*.

As the gene having the higher expression activity in the mammalian cell than the luciferase gene derived from *Photinus Pyralis*, used in the present invention, luciferase derived from click beetles produced in Brazil belonging to genus *Pyrearinus* (e.g., *Pyrearinus termitilluminans*) is particularly preferable. Luciferase belonging to genus *Pyrophorus* (e.g., *Pyrophorus punctatissimus*) produced in Brazil is also preferable.

In particular, luciferase derived from *Pyrearinus termitilluminans* has no variation of luminescence spectrum depending on the pH value, and has a maximum luminescence wavelength of 538 nm. This corresponds to a maximum region in a quantum efficiency of a photomultiplier (PMT) or a charged-coupled device (CCD) camera generally used upon detecting luminescence by luciferase. Thus, luminescence can be detected with good sensitivity.

Luciferase used in the present invention includes not only naturally occurring luciferases but also mutant luciferases having one or two or more substitutions, additions, deletions or insertions of amino acids, and higher expression activity in the cell (particularly the mammalian cell) than luciferase derived from *Photinus Pyralis*. Also, luciferase may be a fusion protein that is fused a second protein to an N terminus or a C terminus.

The "stringent condition" refers to a condition where a specific hybridization occurs, and non-specific hybridization does not. Such a condition is typically about "1×SSC and 0.1% SDS at 37° C.", preferably about "0.5×SSC and 0.1% SDS at 42° C." and more preferably about "0.2×SSC and 0.1% SDS at 65° C.". DNA obtained by hybridization typically has a high homology to DNA represented by the base sequence described in SEQ ID NO: 2. The high homology indicates 80% or more homology, preferably 85% or more homology, more preferably 90% or more homology, particularly 95% or more or 98% or more homology.

The mammals in the present invention include humans, cattle, horses, sheeps, monkeys, swines, mice, rats, hamsters, guinea pigs, rabbits and dogs, and are preferably humans.

The pH-insensitivity means that the variation in the maximum luminescence wavelength of luciferase is 3 nm or less, preferably 2 nm or less, more preferably 1 nm or less and particularly 0.5 nm or less even when the pH value is changed in the cell (particularly the mammalian cell). If the change amount of the maximum luminescence wavelength is in this range, when the expression amounts of the multiple luciferases are quantified by separating luminescence with optical filter, the transmission coefficient of the mutual luminescent proteins is scarcely changed. This is thus preferable.

When the cell (e.g., the mammalian cell) is transformed with the gene construct of the present invention, the transformed cell can obtain significantly high luminescence. When the heteroprotein or the tag is fused, luminescence decreases. Thus, in the conventional gene construct with an insufficient luminescence amount even when nothing is fused, it was difficult to fuse the heteroprotein or the tag. Meanwhile, in the present invention, luciferase to which the heteroprotein or the tag is fuse exhibits a very high amount of luminescence, and thus the imaging in the individual cell can be performed while fusing the heteroprotein or the tag.

The heteroprotein to be fused to the luciferase of the present invention includes an optional heteroprotein. The tag includes protein destabilizing signals encoded by a nucleotide sequence encoding a PEST sequence or ubiquitin or biologically active fragments thereof or mutants or derivative thereof, and intracellular localization signals such as nuclear localization signals, membrane localization signals, cytoplasmic localization signals, mitochondrial localization signals and ER localization signals.

For the destabilization of luciferase, the PEST sequence that destabilizes the luciferase protein may be used, or luciferase mRNA may be destabilized by deleting a poly-A signal or ligating the sequence derived from various genes of c-fos, c-jun, c-myc, GM-CSF, IL-3, TNF-a, IL-2, IL-6, IL-8, IL-10, urokinase, bcl-2, Cox-2 and PAI-2.

By destabilizing the luciferase protein or mRNA, it is possible to precisely observe (with no time lag) the change in the amount of luciferase expressed by the response to a certain stimulation. This was realized for the first time by the gene construct of the present invention exhibiting the higher expression efficiency in the mammalian cell than the gene construct derived from the firefly.

The PEST sequence used as the tag is preferably a 3'-terminus of ornithine decarboxylase or the mutant thereof. The 3'-terminus of ornithine decarboxylase or the mutant thereof is preferably derived from mammals, and generally one most frequently used is derived from mice (SEQ ID NOS: 7 and 8). PEST indicates an amino acid sequence in which proline (P), glutamic acid (E), serine (S) and threonine (T) are rich, and the protein containing the PEST sequence is known to have a short half life.

In one embodiment of the present invention, a luciferase split assay is performed in which luciferase is divided into two, e.g., an N terminal region and a C terminal region, DNA encoding each region is linked to the heteroprotein and their gene constructs are co-expressed in one cell. Here, the N terminal region of luciferase and the C terminal region of luciferase are independently expressed, but a light-emitting design when these are closely located is possible.

First gene construct: (N terminal region of luciferase)-(First Heteroprotein)

Second gene construct: (C terminal region of luciferase)-(Second heteroprotein)

When these gene constructs are co-expressed in one cell, it becomes possible to confirm by the luminescence signal that the C terminal region and the N terminal region are closely located by the interaction between two heteroproteins.

For the luciferase split assay, a successful example using firefly luciferase is reported above in Non-patent Literature 2; click beetle-derived luciferase has greater expression activity than firefly luciferase and is pH-insensitive, and thus is a more suitable probe for use.

For example, the N terminal region and the C terminal region in click beetle-derived luciferase can be designed as follows. The structure of click beetle-derived luciferase has not been demonstrated; however, firefly luciferase, which is similar to beetle luciferase, is known to be comprised of two domains of the large N terminal region comprised of β-barrel and two β-sheets and the C terminal region sandwiching an active center (Conti, E. et al., Crystal structure of firefly luciferase throws light on a superfamily of adenylate-forming enzymes. Structure, 1996 March; 4 (3):287-98). The split assay of firefly luciferase is known to divide at a flexible site that links the two regions; one example thereof is to divide between the amino acid at position 437 and the amino acid at position 438 of the firefly luciferase to make the N terminal region and the C terminal region (Non-Patent Literature 2). According to a homology search of click beetle luciferase and firefly luciferase, the relatively high homology is conserved in the region around the sites linking the N terminal region and the C terminal region. The sites linking the N terminal region and the C terminal region in click beetle luciferase are presumed to be the sites at positions 432 to 436 in the amino acid sequence, and it is preferable to divide here. It is particularly preferable to divide between the sites at positions 433 and 434, and the gene construct is preferably obtained by using the amino acid sequence until the position 1299 in SEQ ID NO: 2 as the N terminal region of luciferase, and the amino acid sequence after the position 1300 in SEQ ID NO: 2 as the C terminal region.

The combination of the first heteroprotein and the second heteroprotein subjected to detecting the interaction of two proteins includes the followings.

TABLE 1

| First heteroprotein | Second heteroprotein |
|---|---|
| FRB | FKBP12 |
| Cdc25C | 14-3-3e |
| STAT1 | mdm2 |
| Fos | Jun |
| Insulin receptor substrate (IRS-1)(Tyrosine phosphorylation domain) | P85 subunit of phosphatidyl inositol (N-terminal SH2 domain) |
| Insulin growth factor-1 receptor, or Insulin receptor | Protein tyrosine phosphatase 1B |

In the present invention, the transcription control of the sequence to be tested is monitored by introducing the gene construct ligating the sequence to be tested having or likely having transcriptional activity (promoter activity) upstream of the luciferase gene into the cell, or using the cell in which the luciferase gene has been incorporated under the transcriptional control sequence of a certain gene by homologous recombination, using luciferase expressed under the transcriptional control of the sequence to be tested as an indicator. For example, in order to measure the transcriptional activity in the mammalian cell, it is possible to arrange a Kozak sequence upstream of the initiation codon to make the translational efficient and arrange the polyadenylation signal downstream of the luciferase gene so that the luciferase gene can be stably expressed. It is more preferable to maximally eliminate the effect of the sequence other than the sequence to be tested on the expression by arranging a transcription termination signal upstream of the transcriptional control sequence to be tested arranged upstream of the luciferase gene.

Furthermore, to analyze a dynamic increase and decrease change of the transcriptional activity, if the intracellular lifespan of luciferase is too long, the signal at the ground state becomes high and it is hard to monitor the transcriptional activation. In such a case, by shortening the intracellular lifespan of luciferase, it becomes possible to more clearly analyze the change of the transcriptional activity. The method for shortening the lifespan of luciferase includes the method of fusing a signal sequence that induce protein degradation or a protein destabilizing signal sequence such as an ubiquitination signal sequence or PEST sequence to luciferase.

The method for introducing the gene construct ligating the sequence to be tested having or likely having the transcriptional activity (promoter activity) upstream of the luciferase gene into the cell may be any chemical technique such as a calcium phosphate method, a DEAE-dextran method and a cationic liposome method, biological techniques using an adenovirus vector, a vaccinia virus vector, a retrovirus vector or an HVJ liposome, and physical techniques such as an electroporation, a DNA direct injection and the use of a gene gun. Generally, electroporation and the chemical technique are easily used; however, the gene introduction efficiency varies widely, depending on the type of cells. The present invention is not only applied to cells having high gene introduction efficiency, but is preferably applied to a transcriptional activity measurement test in living cells having low gene introduction efficiency. In the transcriptional activity measurement test by transient gene introduction in the cells having low gene introduction efficiency, when conventional firefly luciferase is used, signal intensity is low and analysis using living cells cannot be performed sufficiently. The transient gene introduction in the present invention indicates that the luciferase gene construct, e.g., a plasmid, is transfected into the cells to be subjected by the above method to use for a cell assay, without performing a step of separating the cells in which the gene has been introduced from the cells in which the gene has not been introduced (selecting the cells in which the gene has been stably integrated into a chromosome). Cells having low gene introduction efficiency include suspended cells, normal cells and primary cultured cells. In particular, human primary cultured cells are used as an in vitro system in various therapeutic fields in the process of drug discovery, and emphasized as a cell assay model extremely close to an individual organism biologically and as a screening tool easily adapted to automation analyses and high throughput analyses. Examples of the human primary cultured cells include, but are not limited to, human dermal microvascular endothelial cells (HMVEC), human epidermal keratinocytes (HEK), human epidermal melanocytes (HEM), human dermal fibroblasts (HDF), human skeletal muscular cells (HSkMC), human umbilical vein endothelial cells (HUVEC), human umbilical artery endothelial cells (HUAEC), human placental epithelial cells (HPIEpC), human umbilical vein smooth muscle cells (HUVSMC), human umbilical artery smooth muscle cells (HUASMC), human coronary artery endothelial cells (HCAEC), human pulmonary artery endothelial cells (HPAEC), human aortic endothelial cells (HAOEC), human cardiac fibroblasts (HCF), human internal thoracic artery endothelial cells (HITAEC), human subclavian artery endothelial cells (HScAEC), human coronary artery smooth muscle cells (HCASMC), human pulmonary artery smooth muscle cells (HPASMC), human aortic smooth muscle cells (HAOSMC), human internal thoracic artery smooth muscle cells (HITASMC), human subclavian artery smooth muscle cells (HScASMC), human chondrocytes (HC), human osteoblasts (HOb), human synovial cells (HFLS, HFLS-OA, HFLS-RA), human bronchial epithelial cells (HBEpC), human lung fibroblasts (HLF), human follicle dermal papilla cells (HFDPC), human preadiposes (HPA) and human mammary epithelial cells (HMEpC).

The present invention is preferably applied to a living cell transcriptional activity measurement assay in a plate format analysis using smaller amounts of samples per one condition. It is necessary to expose various compounds at a wide range of concentrations to the cells and evaluate actions upon the cells for the drug discovery and the toxicity evaluation of the compounds. Therefore, being able to measure small amounts of the sample in the plate format is necessary. In the small amounts of the samples, the total luminescence intensity emitted from the samples are reduced whereas many samples are measured simultaneously and thus a reading time per sample is shortened. However, in the plate format measurement of the present invention, since a specific signal intensity is higher compared with the conventional methods, it is possible to perform the analysis with high sensitivity and high accuracy. Furthermore, in the method of the present invention, luciferin is only added (administered) to the living culture and there is no step of irradiating the excitation light as in fluorescence detection, which causes great damage to the cells. Thus, it is possible to appropriately prolong the culture time period and trace the action upon the cells for a long time.

EXAMPLES

The present invention will be described in more detail in the Examples.

Example 1

Figure 1:
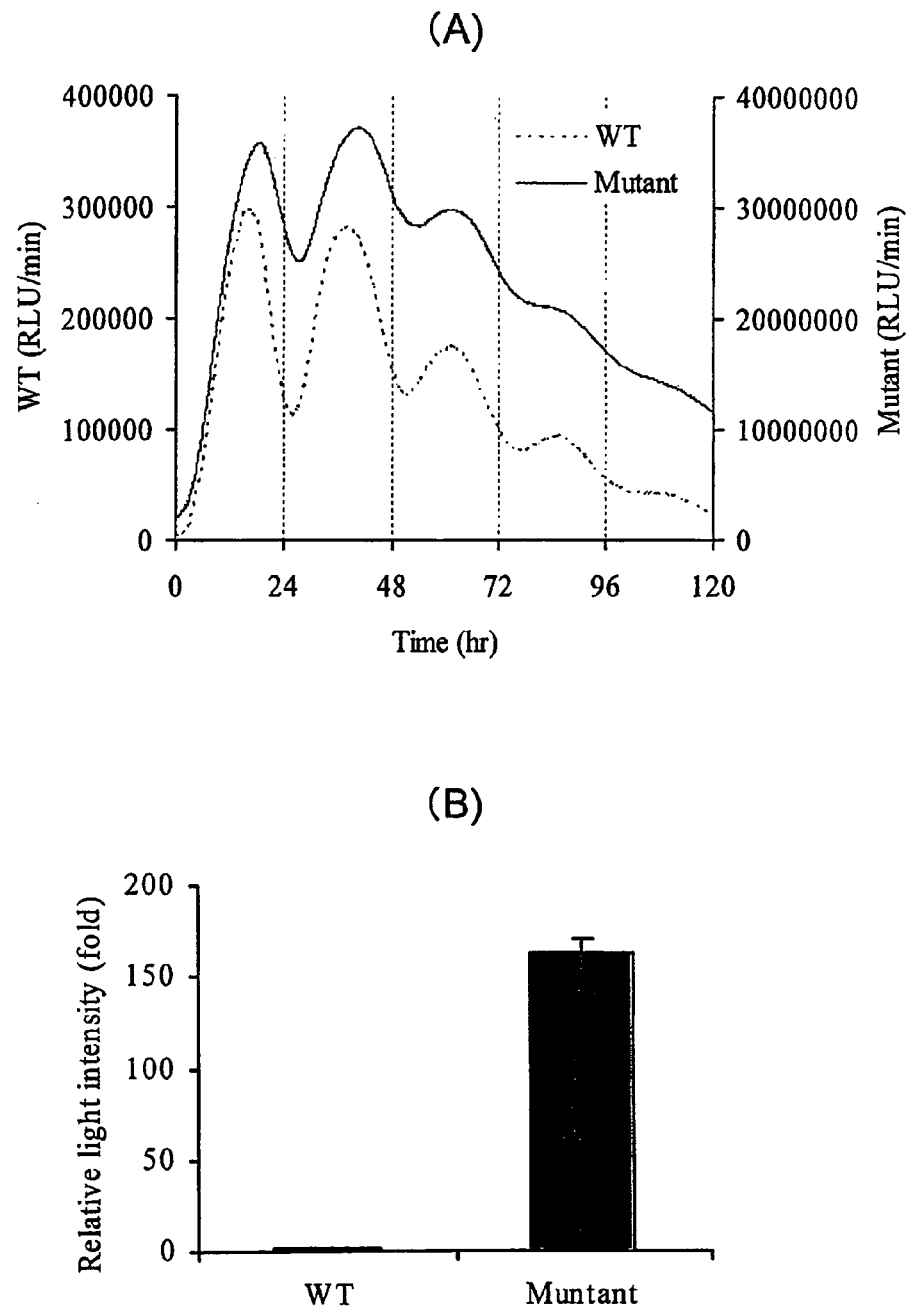
FIG. 1A is a graph showing real-time monitoring of luminescence intensity under the control of Bmal1 promoter as an example using a click beetle luciferase wild type (PtGR; Wild) and a mutant type thereof (PtGRm; mutant)
FIG. 1B is a graph showing a transient assay for Bmal1 promoter transcriptional activity using the click beetle luciferase wild type (PtGR; Wild) and the mutant type thereof (PtGRm; mutant)

Short lifespan-type luciferase was made by ligating a PEST sequence (SEQ ID NO: 7) of murine ornithine decarboxylase to a wild-type (SEQ ID NO: 1) and improved-type (SEQ ID NO: 2) click beetle luciferase cDNA. Vectors in which these had been inserted downstream of a murine circadian clock gene Bmal1 promoter (GenBank Accession No. AB064982) were made. Subsequently, 1 µg of each vector was introduced into cultured fibroblast NIH3T3 cells seeded in a 35 mm culture dish by a lipofection method (LipofectAMINE PLUS, Invitrogen), and the cells were cultured at 37° C. for 24 hours and treated with a DMEM medium containing 100 nM dexamethasone for 2 hours. The medium was replaced with a DMEM medium containing 200 µM D-luciferin and 10% (w/v) bovine serum, and then one minute of luminescence was measured every 15 minutes for 5 days in real time using a real-time gene expression measurement apparatus (AB2500 supplied from ATTO Corporation) (FIG. 1A). The change in about a 24-hour cycle depending on the Bmal1 promoter can be monitored in both wild-type and improved luciferases, but it was found that the luminescence intensity of improved-type luciferase was about 100 times higher than that of wild-type luciferase.

The aforementioned reporter vector (200 ng) was introduced into the cultured fibroblast NIH3T3 cells seeded in a 24-well plate by the lipofection method, the cells were cultured at 37° C. for 24 hours, and disrupted with 300 µL of a cell lysis agent (cultured cell lysis agent for PicaGene Dual Seapansy supplied from Toyo Ink MFG Co., Ltd.). A luminescent substrate solution (50 µL) (PicaGene luminescence reagent II) was added to a cell extract solution (50 µL), and 20 seconds of luminescence was measured using a luminometer (AB2250 supplied from ATTO Corporation) (FIG. 1B). It was found that the luminescence intensity of improved-type luciferase was about 150 times higher than that of wild-type luciferase.

Example 2

Figure 2:
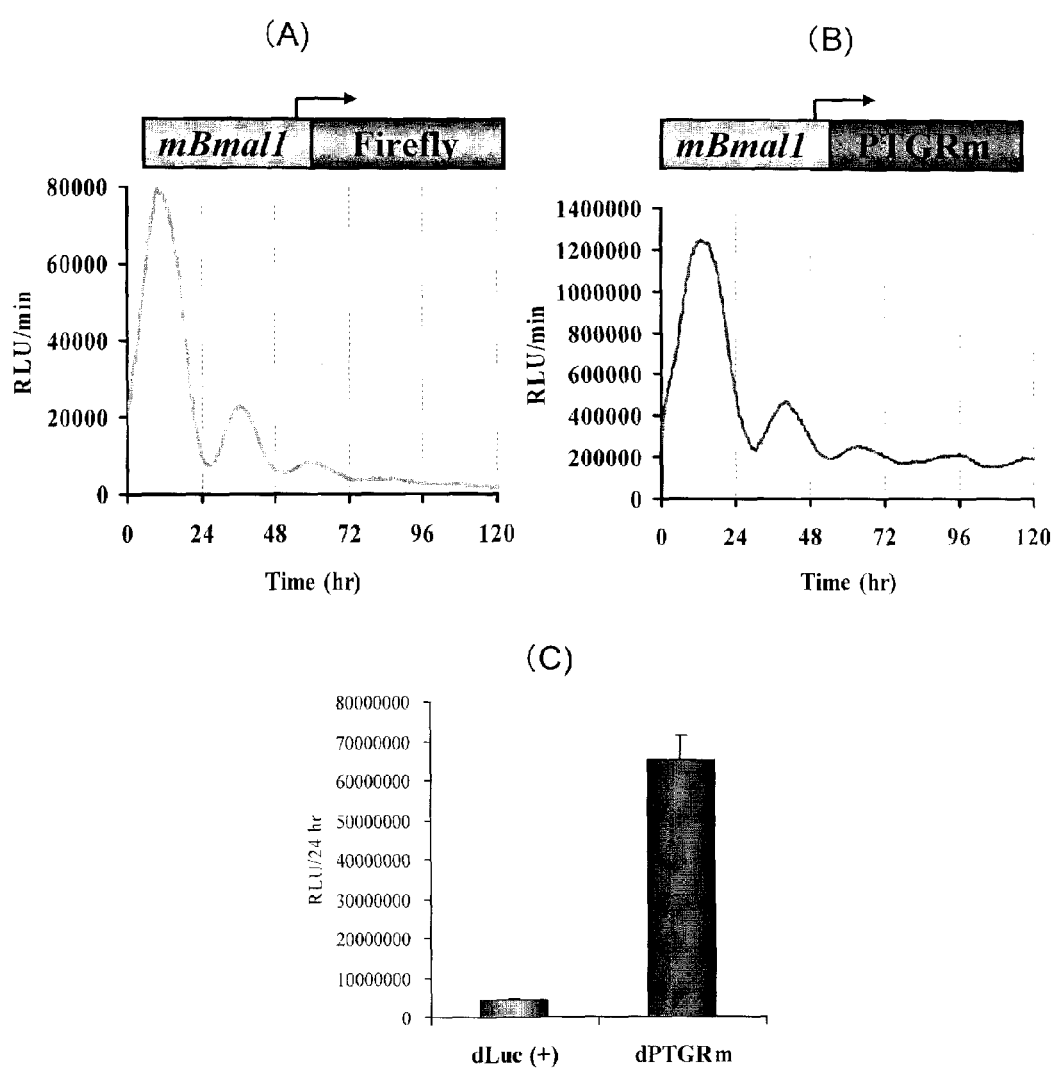
FIG. 2A is a graph showing real-time monitoring of the luminescence intensity under the control of the Bmal1 promoter as the example using luciferase (Firefly) derived from a firefly produced in the US.
FIG. 2B is a graph showing real-time monitoring of the luminescence intensity under the control of the Bmal1 promoter activity as the example using the click beetle luciferase mutant type (PtGRm)
FIG. 2C is a graph showing the results of measuring the Bmal1 promoter activity using the click beetle luciferase mutant type (dPTGRm) and luciferase derived from the firefly produced in North America (dLuc(+))

Short lifespan-type luciferase was made by ligating the PEST sequence (SEQ ID NO: 7) of murine ornithine decarboxylase to firefly luciferase cDNA (Luc(+), supplied from Promega) derived from *Photinus pyralis* produced in North America and improved-type click beetle luciferase cDNA (SEQ ID NO: 2). Vectors in which these had been inserted downstream of a murine circadian clock gene Bmal1 promoter (GenBank Accession No. AB064982) were made. Subsequently, 1 µg of each vector was introduced into cultured fibroblast rat1 cells seeded in a 35 mm culture dish by the lipofection method (LipofectAMINE PLUS), and the cells were cultured at 37° C. for 24 hours and treated with the DMEM medium containing 100 nM dexamethasone for 2 hours. The medium was replaced with a DMEM medium containing 200 µM D-luciferin and 10% (w/v) bovine serum, and then one minute of luminescence was measured every 15 minutes for 5 days using the real-time gene expression measurement apparatus (AB2500 supplied from ATTO Corporation) (FIG. 2). When firefly luciferase derived from *Photinus pyralis* produced in North America (FIG. 2A) was compared with improved-type click beetle luciferase (FIG. 2B), it was found that a change pattern of the luminescence in both luciferase was similar and improved-type click beetle luciferase had an ability equivalent to firefly luciferase derived from *Photinus pyralis* produced in North America used for the real-time analysis. Meanwhile, as a result of integrating the luminescence amount within 24 hours (FIG. 2C), it was found that the luminescence intensity of improved-type click beetle luciferase was 15 times or more higher than that of firefly luciferase derived from *Photinus pyralis* produced in North America.

Example 3

Figure 3:
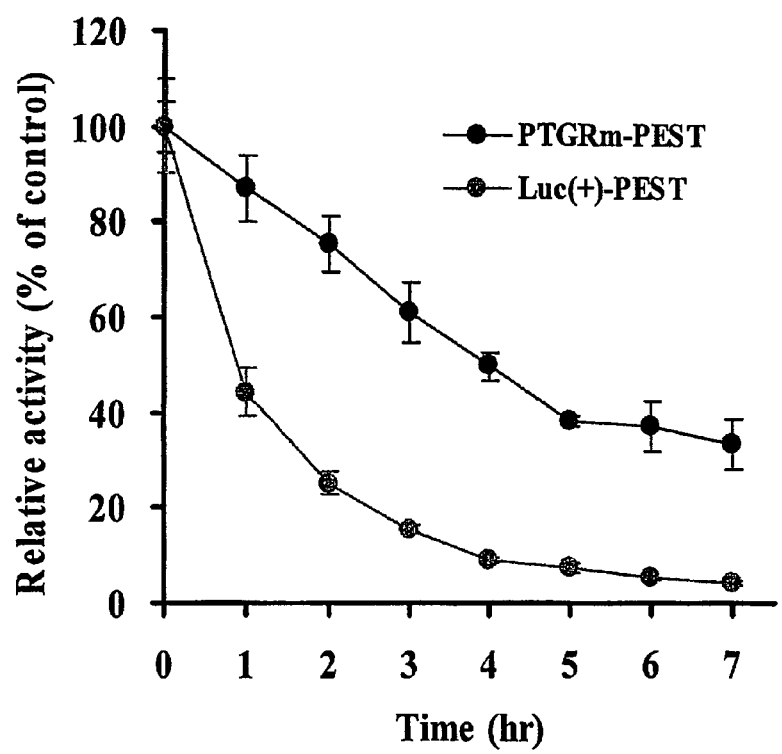
FIG. 3 is a graph showing an intracellular half life of the click beetle luciferase mutant type (PtGRm-PEST) and luciferase derived from the firefly produced in North America (dLuc(+)-PEST)

Expression vectors were made by inserting the aforementioned short lifespan-type firefly luciferase cDNA and short lifespan-type improved-type click beetle luciferase cDNA downstream of an SV40 promoter. The expression vector (200 ng) was introduced into the cultured fibroblast NIH3T3 cells seeded in a 24-well plate by the lipofection method, and the cells were cultured at 37° C. for 48 hours. Subsequently, the medium was replaced with the medium containing 100 µM protein synthesis inhibitor, cycloheximide, and after culturing for 30 minutes, the intracellular luminescence intensity was measured every one hour. The luminescence intensity was measured in the same way as in Example 1 (FIG. 3). In short lifespan-type firefly luciferase derived from *Photinus pyralis* produced in North America, the half life was one hour; however, in short lifespan-type improved click beetle luciferase, the half life was 4 hours, a fourfold extension.

Example 4

Figure 4:
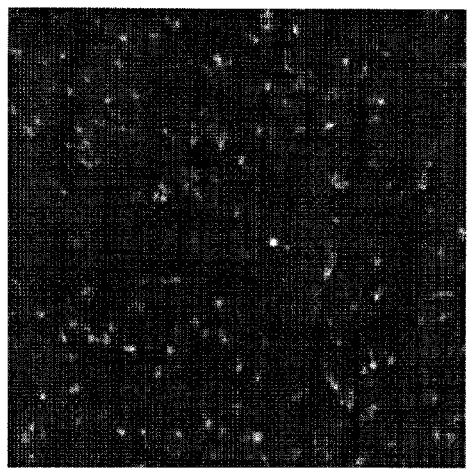
FIG. 4 is a series of photographs showing bioluminescence imaging of mammalian cells expressing (A) luciferase derived from the firefly produced in North America (Firefly) and (B) the click beetle luciferase mutant type (PtGRm)
Figure 4:
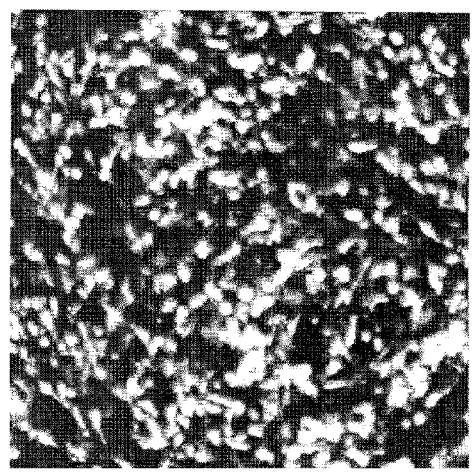

A FLAG tag sequence (MDYDDDDK; SEQ ID NO: 15) was ligated to the N terminus of the firefly luciferase cDNA (Luc(+), supplied from Promega) derived from *Photinus pyralis* produced in North America and the improved-type click beetle luciferase cDNA (SEQ ID NO: 2). The expression vector (2 µg) obtained by inserting one of them downstream of the CMV promoter was introduced in the cultured fibroblast NIH3T3 cells by the lipofection method, and the cells were cultured at 37° C. for 24 hours. Subsequently, the medium was replaced with a DMEM medium containing 200 µM D-luciferin and 10% (w/v) bovine serum, and three minutes of bioluminescence was measured using a CCD camera (Cellgraph supplied from ATTO Corporation) cooled to −60° C. When firefly luciferase derived from *Photinus pyralis* produced in North America (FIG. 4A) was compared with improved-type click beetle luciferase (FIG. 4B), it was found that the mammalian cells producing click beetle luciferase clearly emit strong signals. When the cells were observed by increasing magnification, it was found that no bioluminescence was observed in the nuclei, and that by the PEST sequence, luciferase was localized in the intracellular cytoplasm, which emits light.

Example 5

The improved click beetle luciferase cDNA (SEQ ID NO: 2) inserted downstream of the CMV promoter was identified to be localized in peroxisomes in the mammalian cells. Improved click beetle luciferase to be localized in the cytoplasm was made by deleting the amino acid sequence SKL at the C terminus of this cDNA. Subsequently, improved click beetle luciferase to be localized in the nucleus was made by arranging a nuclear localization signal sequence DPKKKRKVDPKKKRKVDPKKKRKV (SEQ ID NO: 3) to the C terminus of the improved click beetle luciferase to be localized in the cytoplasm. Additionally, improved click beetle luciferase to be localized in the endoplasmic reticulum was made by arranging the sequence MGWSCIILFLVATAT-GAHS (endoplasmic reticulum localization signal sequence, Vh chain targeting signal; SEQ ID NO: 4) to the N terminus of this improved click beetle luciferase to be localized in the cytoplasm and arranging the sequence SEKDEL (endoplasmic reticulum retention signal; SEQ ID NO: 6) to the C terminus thereof. Furthermore, improved click beetle luciferase to be localized in the membrane was made by arranging the sequence MLCCMRRTKQVEKNDEDQKI (membrane localization signal, Neuromodulin N-terminus; SEQ ID NO: 5) to the N terminus of this improved click beetle luciferase to be localized in the cytoplasm.

All click beetle luciferase cDNA fused to organelle localization signals were inserted downstream of the CMV promoter. The resulting expression vector (0.2 µg) was introduced into the cultured fibroblast NIH3T3 cells by LipofectAMINE PLUS. After culturing the cells at 37° C. for 24 hours, the cells were disrupted with 300 µL of PBS, 50 µL of the luminescent substrate solution (PicaGene luminescent reagent II) was added to 50 µL of the cell extract solution, and the luminescence intensity was measured in the same way as in Example 1. Although the luminescence intensity was changed depending on the localization signal, it was found that all fused luciferase have approximately 20% or more luminescence intensity relative to that of the improved click beetle luciferase of SEQ ID NO: 2, and that they have luminescence intensity while localized in various sites in the cells (FIG. 5).

Example 6

Figure 6:
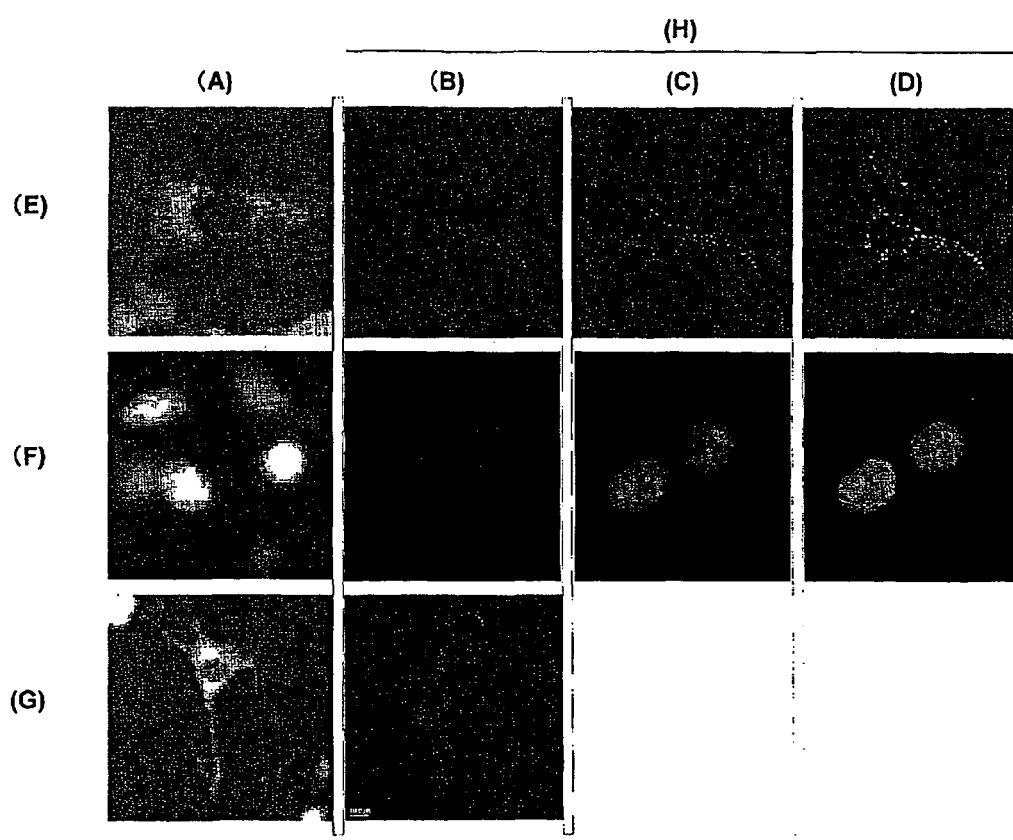
FIG. 6 is a series of photographs comparing bioluminescence imaging and fluorescence imaging of each intracellular organelle.

The expression vectors pCMV-FLAG-PtGRm-POX (to be localized in the peroxisome), pCMV-FLAG-PtGRm-Nuc (to be localized in the nucleus) and pCMV-FLAG-PtGRm-Cyto (to be localized in the cytoplasm) were made by fusing the FLAG tag sequence (MDYDDDDK; SEQ ID NO: 15) to the N terminus of the click beetle luciferases cDNA to be localized in the peroxisome, the nucleus and the cytoplasm and inserting each of them downstream of the CMV promoter. Meanwhile, the expression vector pCMV-EGFP-POX (EGFP to be localized in the peroxisome) was made by fusing the SKL sequence to the C terminus of EGFP (Clontech) cDNA and inserting this downstream of the CMV promoter. Subsequently, the combination of pCMV-FLAG-PtGRm-POX 2 µg and pCMV-EGFP-POX 2 µg, the combination of pCMV-FLAG-PtGRm-Nuc 2 µg and pAcGFP-Nuc (GFP localized in the nucleus, supplied from Clontech) 2 µg, or 2 µg of pCMV-FLAG-PtGRm-Cyto was introduced into the cultured fibroblast NIH3T3 cells seeded in the 35 mm dish by the lipofection method (LipofectAMINE PLUS supplied from Invitrogen), and the cells were cultured at 37° C. for 24 hours. For the bioluminescence imaging, after replacing with DMEM medium containing 200 µM D-luciferin and 10% bovine serum, three minutes of luminescence was photographed using a bioluminescence imaging apparatus (Cellgraph supplied from ATTO Corporation) mounting the cooled CCD camera with a 40× objective lens. The intracellular localization of improved click beetle luciferase was observed by immunostaining using an anti-FLAG antibody (Sigma). The intracellular localization of co-transfected GFP was observed by GFP fluorescence using a confocal microscope (Bio-Rad) (FIG. 6). By immunostaining using the anti-FLAG antibody and the fluorescence imaging by the localized GFP, it was identified that improved click beetle luciferase to be localized in the peroxisome, the nucleus and the cytoplasm were localized in each organelle. Meanwhile, by the bioluminescence imaging using the objective, high magnification lens, the remarkable bioluminescence signal emitted from each organelle was obtained in the three-minute exposure, and it was demonstrated that the imaging of each signal localized in each organelle was possible in the cell.

Example 7

Figure 7:
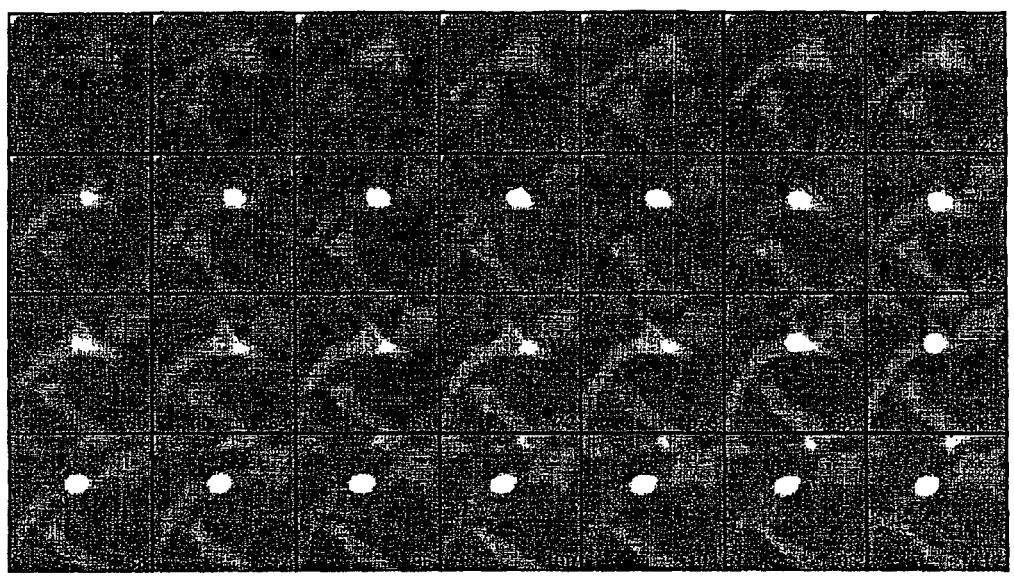
FIG. 7 is a series of photographs showing bioluminescence imaging photographed every 4 minutes.

An expression vector was made by fusing murine importin a1 cDNA (GenBank No. D55720) to the N terminus of improved clock beetle luciferase to be localized in the cytoplasm and inserting this downstream of the CMV promoter. Subsequently, 2 μg of the vector was introduced into the cultured fibroblast NIH3T3 cells seeded in the 35 mm dish by the lipofection method (LipofectAMINE PLUS), the cells were cultured at 37° C. for 3 hours, and the medium was replaced with DMEM medium containing 200 μM D-luciferin and 10% (w/v) bovine serum. For the luminescence imaging, three minutes of luminescence was photographed in the exposure every 4 minutes using the bioluminescence imaging apparatus (Cellgraph supplied from ATTO Corporation) with the 40× objective lens (FIG. 7). By the bioluminescence imaging, it was identified that transport of importin a1 between the nucleus and the cytoplasm was repeated about every 30 minutes, and it was found that the change in the intracellular localization of the protein can be imaged continuously.

Example 8

Construction of Plasmid Containing AP1 Response Sequence and NFκB Response Sequence A promoter sequence derived from Herpes simplex virus thymidine kinase (HSVtk) was amplified using pSLG-HSVtk control (Toyobo Co., Ltd.) as a template and using oligonucleotides 1, 2 (Sigma Aldrich Japan) (SEQ ID NOS: 9 and 10) and PCR enzyme KOD-plus-(Toyobo Co., Ltd.). Recognition sequences for restriction enzymes SpeI or EcoRV are added to the 5'-terminus of the oligonucleotide, respectively. This PCR product and pELuc-test (Toyobo Co., Ltd., vector carrying PtGRm gene of SEQ ID NO: 2) were digested with the restriction enzymes SpeI and EcoRV (Toyobo Co., Ltd.), and ligated using Ligation high (Toyobo Co., Ltd.) to insert the HSVtk promoter upstream of the PtGRm gene in pELuc-test (pPtGRm-HSVtk). Subsequently, the oligonucleotide 3 (Sigma Aldrich Japan) (SEQ ID NO: 11) and the oligonucleotide 4 (Sigma Aldrich Japan) (SEQ ID NO: 12) complementary thereto, the oligonucleotide 5 (Sigma Aldrich Japan) (SEQ ID NO: 13) and the oligonucleotide 6 (Sigma Aldrich Japan) (SEQ ID NO: 14) complementary thereto were annealed to make an NFκB response sequence cassette and an AP1 response sequence cassette.

Figure 8:
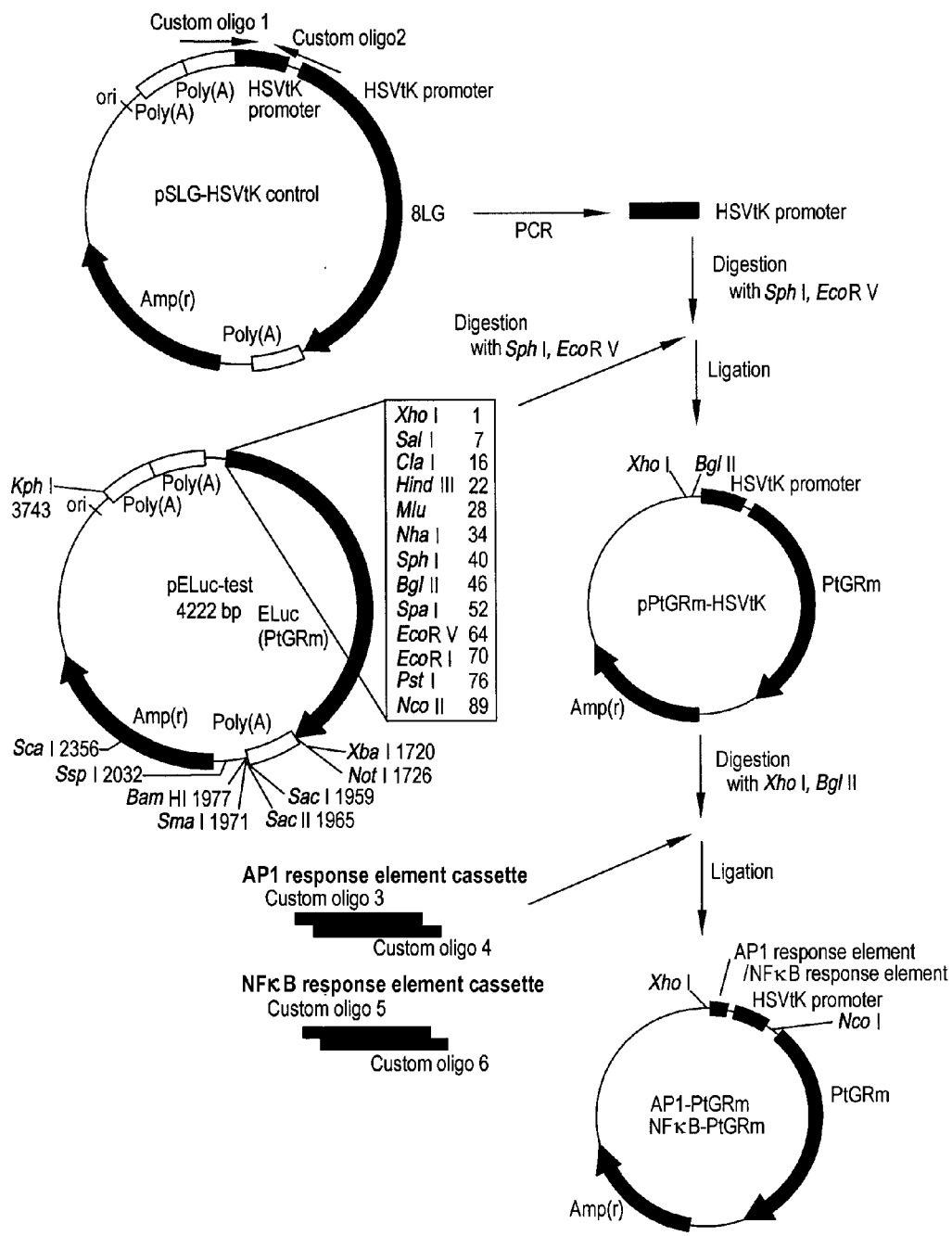
FIG. 8 is a view showing a flow for constructing a plasmid comprising an AP1 response sequence and an NFκB response sequence used in Examples.

Each cassette is constructed to form complementary chains to cleavage sites of the restriction enzyme XhoI at one end and the restriction enzyme BglII at the other end. pPtGRm-HSVtk was digested with the restriction enzymes XhoI and BglII (Toyobo Co., Ltd.), the cassette was inserted upstream of the HSVtk promoter (NFκB-PtGRm, AP1-PtGRm; FIG. 8). Subsequently, NFκB-PtGRm and AP1-PtGRm were digested with the restriction enzymes XhoI and NcoI (Toyobo Co., Ltd.), and the regions of NFκB response sequence+HSVtk promoter+Kozak sequence and the region of AP1 response sequence+HSVtk promoter+Kozak sequence were cut out. Meanwhile, pGL3-Basic (Promega, vector carrying firefly luciferase Luc(+)) was treated with the restriction enzymes XhoI and NcoI, and the region of NFκB response sequence+HSVtk promoter+Kozak sequence or the region of AP1 response sequence+HSVtk promoter+Kozak sequence was inserted upstream of the firefly luciferase gene (NFκB-Luc (+), pGL3-AP1-Luc(+)).

It is known that AP1 is an abbreviation of activator protein complex 1 and a series of transcription factor complexes composed of c-Jun, c-Fos and the like, and that it promotes the gene expression by binding to an AP1 response sequence motif (TGACTCA) conserved in the promoter region of many genes (collagenase, metallothionein IIA, stromelysin) induced by phorbol ester (TPA). NFκB is known as the transcription factor involved in TNFα and inflammatory stimulation.

Example 9

Analysis of AP1 Response Sequence in HeLa S3 Cells

Figure 9:
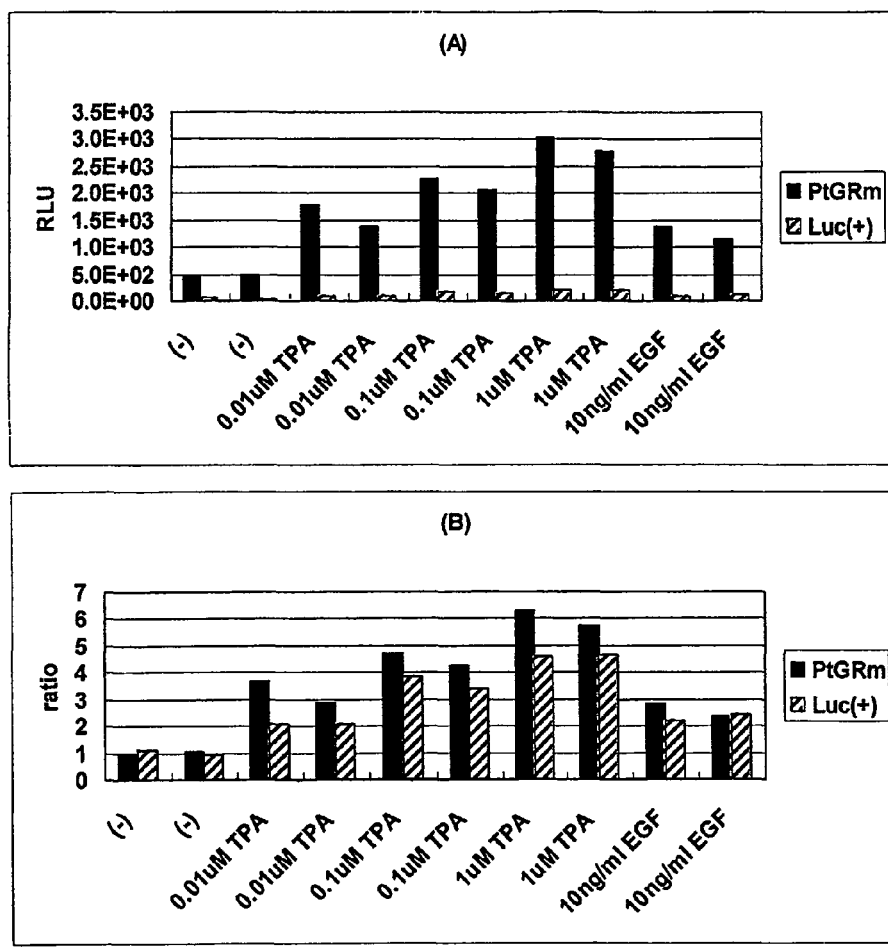
FIG. 9 is a series of graphs showing data comparing expressions of luciferase gene linked to the AP1 response element in HeLa S3 cells under each condition, (A) measurement values and (B) induction ratios.

HeLa S3 cells were seeded at 3×10$^4$ cells (100 μL) per well in a 96-well white opaque plate, and cultured in Dulbecco's Modified Eagle's Medium DMEM (Nissui Pharmaceutical Co., Ltd.) containing 10% FCS. The following day, 0.2 μg per well of the plasmid pELuc-AP1 or pGL3-AP1 (diluted with 25 μL of DMEM containing no FCS) and 0.5 μL of Lipofectamine 2000 transfection reagent (Invitrogen, diluted with 25 μL of DMEM)) were mixed and added to the cells in the medium replaced with 100 μL of DMEM+0.1% FCS, which was incubated for 24 hours to introduce the gene. The following day, the medium was either not replaced, or replaced with DMEM+0.1% FCS (further containing 0.2 mM D-luciferin) containing 0.01 μM TPA (Sigma), 0.1 μM TPA, 1 μM TPA or 10 ng/mL of EGF, and the cells were incubated for 5 hours. Subsequently, the luminescence was measured using a plate reader 1420 ARVOMX (Perkin Elmer). The results are shown in FIG. 9. In the graph for measurement values, readout values were plotted, and in the graph for induction ratios, an expression induction ratio at each concentration calculated when the value in an additive-free condition equaled 1 was plotted. In the luciferase of the present invention, the same variation as that in conventional luciferase was observed in each stimulation, whereas a luminescence intensity 15 times higher was observed.

Example 10

Analysis of NFκB Response Sequence in Jurkat Cells

Jurkat cells at 1×10$^6$ cells (4 mL) were suspended in RPMI 1640 medium containing 0.1% FCS (Nissui Pharmaceutical Co., Ltd.), and 1 mL per well was dispensed in 4 wells in a 24-well plate. Each 2 μg of plasmids, pELuc-NFκB or pGL3-NFκB and pELuc-AP1 or pGL3-AP1 (diluted with 200 μL of RPMI 1640 containing no FCS) were mixed with LipofectAMINE 2000 (diluted with 200 μL of RPMI 1640 containing no FCS), and then mixed with Jurkat cells, which were incubated for 24 hours to introduce the genes. The following day, 50 μL of gene-introduced Jurkat cells were dispensed in a white transparent plate. Either nothing was added, or 50 μL of RPMI 1640+0.1% FCS (further containing 0.1 nM D-luciferin) containing TNFα (PEPROTEVH) at various concentrations was added to the Jurkat cells in which pELuc-NFκB or pGL3-NFκB and pELuc-AP1 or pGL3-AP1 had been introduced, and the cells were incubated for 5 hours. TNFα was added at a final concentration of 0.01 ng/mL, 0.1 ng/mL, 1 ng/mL or 10 ng/mL. Subsequently, the luminescence was measured using the plate reader 1420 ARVOMX (Perkin Elmer).

Figure 10:
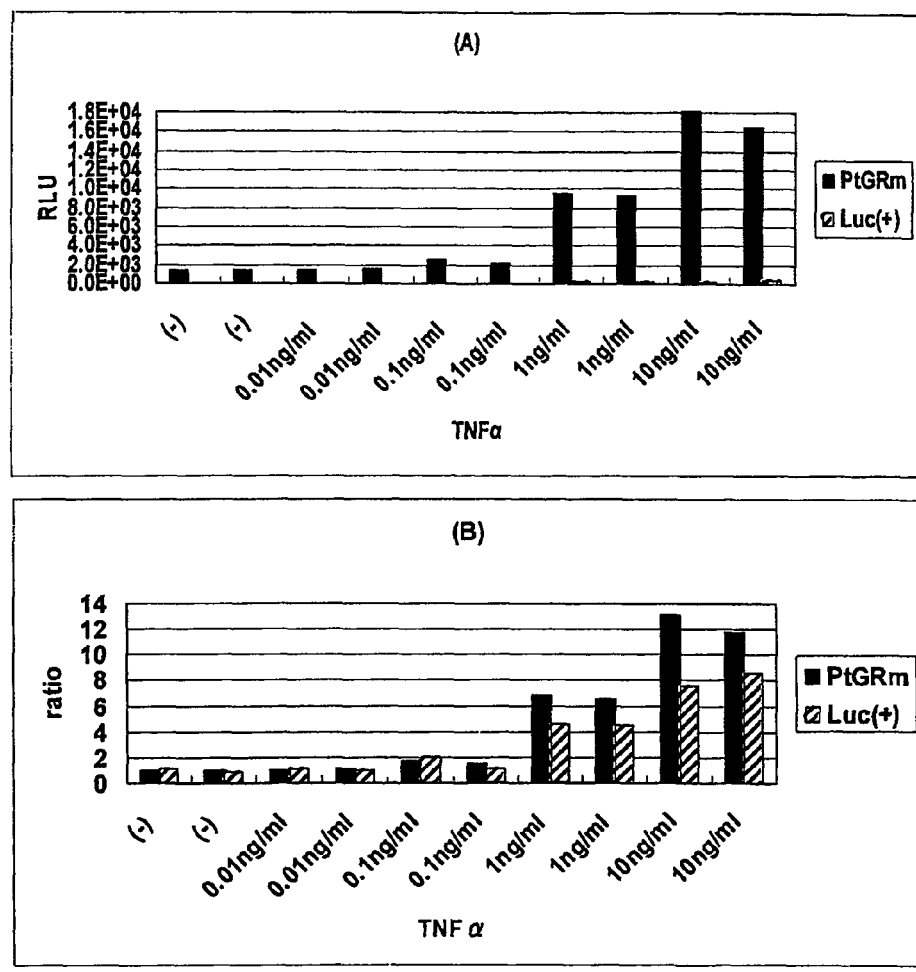
FIG. 10 is a series of graphs showing data comparing expressions of luciferase linked to the NFκB response element in Jurkat cells under each condition, (A) measurement values and (B) induction ratios.

The results of examining the changes for the stimulation with TNFα using the construct containing the NFκB response sequence are shown in FIG. 10. In the graph for measurement values, the readout values were plotted, and in the graph for induction ratios, the expression induction ratio at each concentration calculated when the value in the additive-free condition equaled 1 was plotted. In the measurement of the transcriptional activity using the click beetle luciferase of the present invention, the changes of the luminescence equivalent to or higher than those in the measurement using conventional luciferase were also observed whereas a luminescence intensity approximately 30 to 60 times higher was observed.

Figure 11:
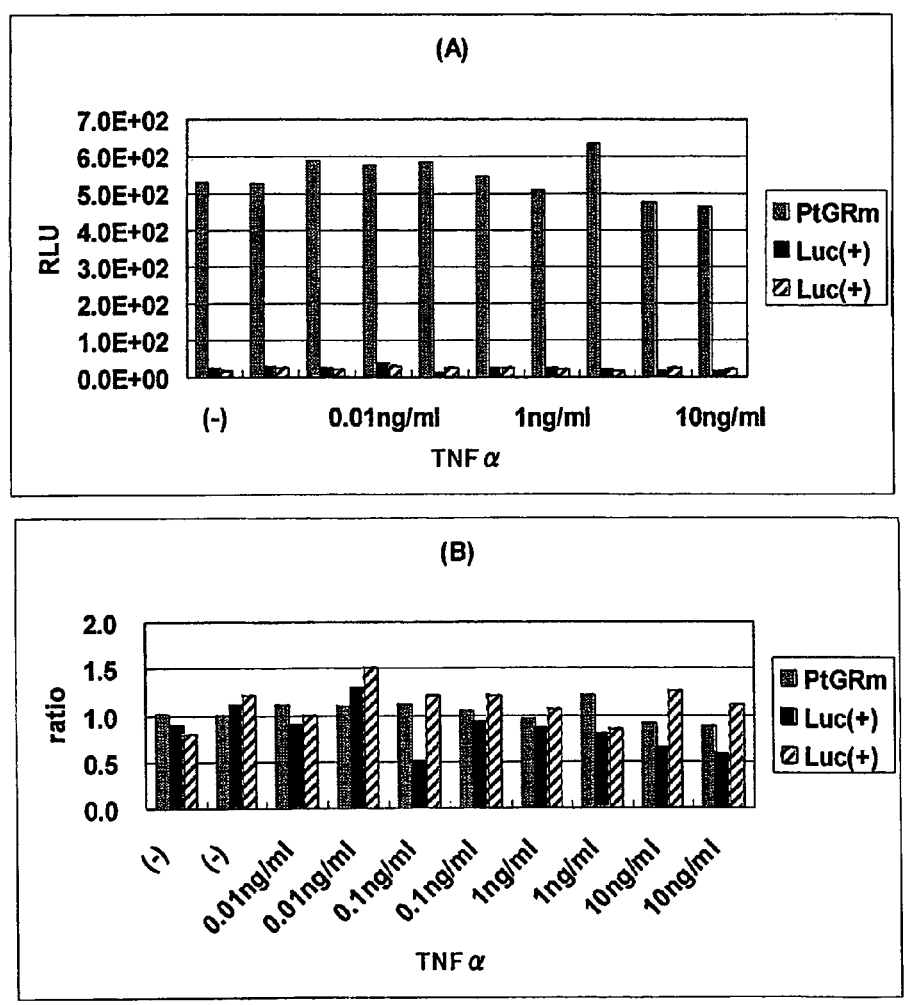
FIG. 11 is a series of graphs showing data comparing expressions of luciferase linked to the AP1 response element in Jurkat cells under each condition, (A) measurement values and (B) induction ratios.

The results of examining the changes for the stimulation with TNFα using the construct containing the AP1 response sequence are shown in FIG. 11. In the graph for measurement values, the readout values were plotted, and in the graph for induction ratios, the expression induction ratio at each concentration calculated when the value in the additive-free condition equaled 1 was plotted. In the measurement of the transcriptional activity using the click beetle luciferase of the present invention, a signal intensity approximately 20 to 30 times higher than the measurement using firefly luciferase was observed. In the method of the present invention, no significant change for each stimulation was observed as was the case with conventional luciferase, whereas the values in the firefly luciferase method varied widely. Thus, it was confirmed in the method of the present invention that a more highly accurate analysis was possible in the analysis of the sequence to be assayed having the low gene introduction efficiency and the low transcriptional activity.

Example 11

Luciferase Derived from Click Beetle

A click beetle-derived luciferase enzyme preparation was acquired as a recombinant body by inserting the luciferase gene PtGRm in the vector pELuc-test (Toyobo Co., Ltd.) into the expression vector for *Escherichia coli* and expressing it in *Escherichia coli*. As a firefly luciferase enzyme preparation, QuantiLum Recombinant Luciferase (Promega, described as fLuc in the figure) was used. For each enzyme preparation, a luminescence reagent containing 15 mM $MgSO_4$, 6 mM EDTA, 4 mM Co-enzyme A, 1.2 mM D-luciferin, 6 mM DTT, 0.2% Nonidet P40, 2 mM ATP and 2 μg/mL of the enzyme preparation was prepared. Then, 100 μL of ATP solution at 0.02 nM, 0.2 mM or 1 mM and 100 μL of 100 mM Hepes-NaOH pH 6.6 to 8.8 were mixed, and the luminescence was measured.

Figure 12:
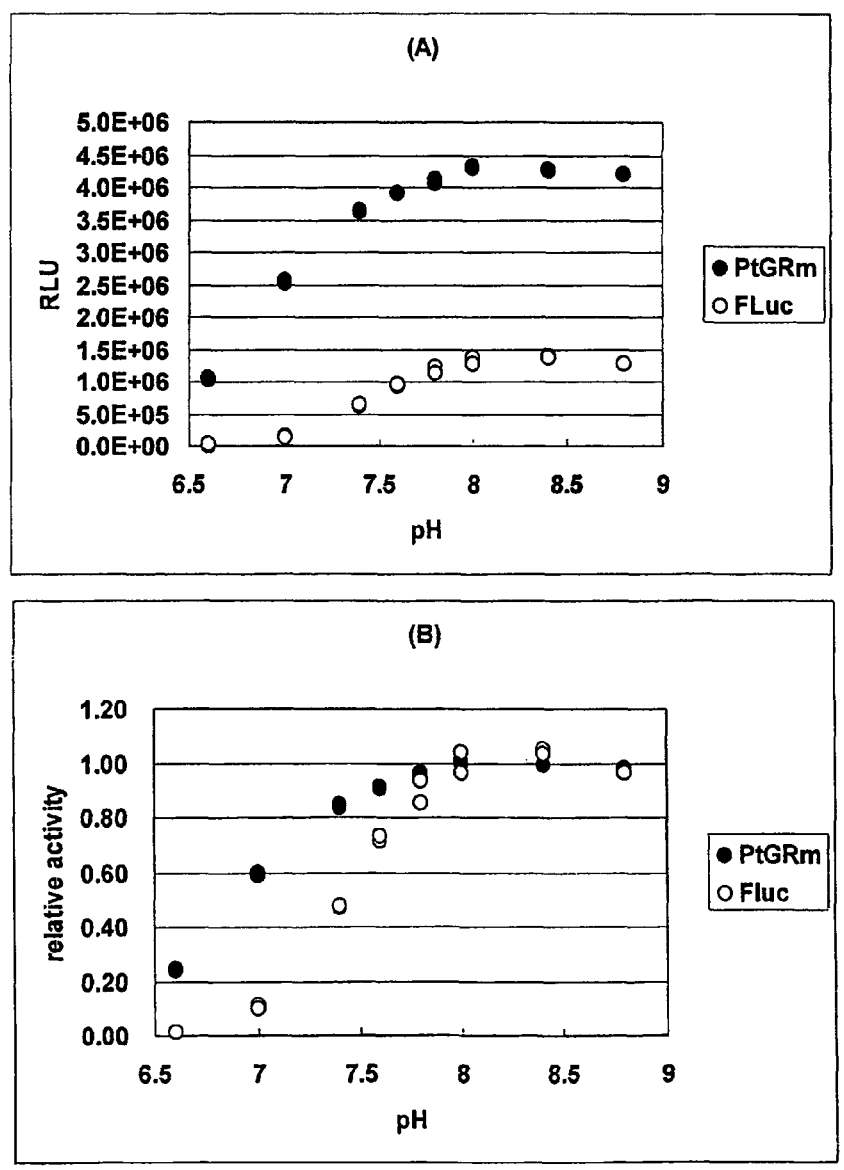
FIG. 12 is a series of graphs of plotting luminescence measurement values at each pH, and a relative activity at each pH when the measurement value at pH 8.0 was 100 in each luciferase; (A) signal intensity and (B) pH dependency of PtGRm and Fluc.

A graph of luminescence measurement values and a graph obtained by plotting the relative activity at each pH when the measurement value at pH 8.0 was set as 100 in each luciferase are shown in FIG. 12. As a result, it was demonstrated that the variation due to the pH values is smaller in click beetle-derived luciferase.

Industrial Applicability

The present invention provides luciferase exhibiting the augmented luminescence intensity for the intracellular imaging. By the use of this enzyme, the ATP distribution and the organelle localization in the cell can be visualized. These can be utilized for the treatment and examination of pathological conditions and drug discoveries.

The present invention provides a method for measuring the transcription activity in the living cell. By the use of the method of the present invention, it becomes possible to perform living cell assays in promoter systems with weak transcriptional activity and in cell systems such as suspension cells and primary cultured cells with low efficiency for the transient introduction of the gene, in which analysis by conventional methods is difficult. Furthermore, the applicable scope of the analysis can be expanded to the plate format using the samples in small amounts. Thus, the method of present invention can be utilized in the analysis of the signal transduction system using the gene transcription as the indicator, or as a screening system for compounds, and greatly contributes to the drug discovery and medical practice industries.

The invention claimed is:

1. An isolated gene construct encoding pH-insensitive click beetle luciferase, wherein the click beetle luciferase is encoded by the nucleic acid sequence of SEQ ID NO: 2.

2. The isolated gene construct according to claim 1, wherein the gene construct encodes a fusion protein comprised of the click beetle luciferase sequence or an N-terminus domain sequence or C-terminus domain sequence thereof, and at least one heteroprotein sequence or tag sequence.

3. The isolated gene construct according to claim 2, wherein the heteroprotein sequence or tag sequence is an intracellular localization signal.

4. An isolated cell comprising the gene construct of claim 1.

5. The cell according to claim 4, wherein the cell is a mammalian cell.

6. The cell according to claim 4, wherein the cell is a human cell.

7. A method for imaging of an intracellular organelle, which method comprises culturing the cell according to claim 4, such that the pH-insensitive click beetle luciferase is expressed, and measuring luminescence by the expressed luciferase in the cell, thereby imaging the intracellular organelle.

8. A method for measuring a transcription activity comprising culturing a test cell which expresses a pH-insensitive click beetle luciferase under control of a transcription control sequence, subjecting the test cell to a test under a desired condition and measuring luminescence by the expressed luciferase in a living cell, wherein the pH-insensitive luciferase gene is encoded by the nucleic acid sequence of SEQ ID NO: 2.

9. The method according to claim 8, wherein the cell is selected from the group consisting of mammalian cells, yeast, *Escherichia coli* and plant cells.

10. The method according to claim 8, wherein the transcription control sequence to be tested is a sequence having a low transcription activity.

11. The method according to claim 8, wherein the cell is a cell having a low gene introduction efficiency.

12. The method according to claim 8, wherein the test cell is cultured in a cell culture medium comprising 0.01 to 10 mM D-luciferin.

13. The method according to claim 8, which is performed in a 96-, 384- or 1,536-well plate format.

14. The method according to claim 8, wherein an effect of a compound on the cell is evaluated by an expression difference of luciferase.

15. An isolated cell comprising the gene construct of claim 2.

16. An isolated cell comprising the gene construct of claim 3.

17. The cell according to claim 15, wherein the cell is a mammalian cell.

18. The cell according to claim 17, wherein the cell is a human cell.

19. The cell according to claim 16, wherein the cell is a mammalian cell.

20. The cell according to claim 19, wherein the cell is a human cell.

* * * * *

SEQUENCE LISTING

<160> NUMBER OF SEQ ID NOS: 18

<210> SEQ ID NO 1
<211> LENGTH: 1632
<212> TYPE: DNA
<213> ORGANISM: Pyrearinus termitilluminans

<400> SEQUENCE: 1

```
atgatgaaga gagaaaaaaa tgttgtttac ggccccgaac ccaaacaccc tttgggaaac      60
tttactgctg gagaaatgct ctacaatgcc cttcataagc attcccacat accgcaagca     120
atattagatg tgatgggtaa tgaatcgctg tcatatcaag aatttttcga cactactgtc     180
aagctaggac aaagtcttca aaattgtgga tacaagatga atgatgtagt gtcgatctgt     240
gctgagaaca ataaaagatt tttcatcccc attatttcag cttggtatat tggtatggtt     300
gtagcacctg ttaatgaaga ctacatccca gatgaacttt gtaaagtcac gggtatatca     360
aaaccaatac tggtcttcac tacaagaaaa atcttaccta aggtattaga ggtaaaggac     420
agaactaatt acataaagag aattataata ctagattctg aagaaaatct gcttggttgc     480
gaaagtcttc ataattttat gtcccgttat tcggataata atcttcagac ctttaagcct     540
ctacattacg atcctgttga tcaagtggca gctattttat gttcgtcagg cacaactgga     600
ttacccaaag gtgttatgca aacgcataga aacatttgtg ttcgacttac acatgcttcg     660
gatcccagag ttggaacaca acttattcct ggagtatcag ttttggcgta tctgcctttc     720
```

| | |
|---|---|
| ttccatgctt ttgggttttc tataaactta ggatacttta tggtgggcct tcgtgttgtt | 780 |
| atgctaagac gatttaatca agaagtattt ttaaaagcca ttcaagatta tgaagttcga | 840 |
| agtgtaatca acgttccatc aacaatactg ttcttgtcga aaagtccttt agttgacaaa | 900 |
| tacgatttat cgactttggc ggaattgtgt tgcggcgctg caccattagc aaaggaagtt | 960 |
| gctgagatag cagtgaaacg actaaacctg ccaggaattc gttgtggata tggtttgaca | 1020 |
| gagtctactt cagctaatat acatactctt cacaatgaat ttaagtcagg atcacttgga | 1080 |
| aaagtcactc cttatatggc tgcgaaaata atagatagga acactggtga agctttggga | 1140 |
| ccaaatcaag ttggagaact atgcatctgg ggtcctatgg taacaaaagg ttacgtgaac | 1200 |
| aatccacaag ccaccaaaga ggctattgat gacgacggtt ggcttcactc tggagacttt | 1260 |
| ggatactatg atgaggatga atatttctat atagtggacc gttacaagga acttattaaa | 1320 |
| tataaaggct atcaggtagc acctgtagaa ttagaagaga ttttattaca acatccaggt | 1380 |
| ataagagatg ttgctgtcgt tggtattcct gatatagaag ctggagaact accagctggg | 1440 |
| ttcgtggtta acaacccgg agcacaactt acagcaaaag aagtttacga ttttcttgcc | 1500 |
| caacgggtct ctcattcaaa gtatttgcgt ggaggagttc gattcgttga ttcaataccc | 1560 |
| aggaatgtta caggtaaaat ttcaagaaaa gaacttcgag aggcgttgat ggaaaaagct | 1620 |
| tctaaacttt aa | 1632 |

<210> SEQ ID NO 2
<211> LENGTH: 1629
<212> TYPE: DNA
<213> ORGANISM: Pyrearinus termitilluminans

<400> SEQUENCE: 2

| | |
|---|---|
| atggagagag agaagaacgt ggtgtacggc cccgagccca gcaccctct gggcaacttc | 60 |
| accgccggcg agatgctgta caacgctctg cacaagcact cccacatccc ccaggccatc | 120 |
| ctggacgtga tgggcaacga gtccctttcc taccaggagt tcttcgacac tactgtgaag | 180 |
| ctgggccaga gcctccagaa ctgtggctac aagatgaacg atgtcgtgtc gatctgtgca | 240 |
| gagaacaaca agagattctt catccccatc atctccgcct ggtacatcgg catggtggtg | 300 |
| gcccctgtga cgaggacta tatcccagac gagctgtgta agtgaccgg catctccaag | 360 |
| ccgatcctgg tcttcaccac taggaagatc ctgcctaagg ttttggaggt taaagacaga | 420 |
| accaactaca taagaggat catcatactg gactctgaag agaacctgct gggctgcgag | 480 |
| agcctgcaca acttcatgtc caggtactcc gacaacaacc tccaaacatt caagcctctg | 540 |
| cactacgacc ctgtggacca ggtagccgcc atcctgtgct cctccggcac aaccggcctg | 600 |
| cctaaaggcg tgatgcagac ccacaggaac atctgtgtga gactcacaca cgcatctgac | 660 |
| cccagagtgg gtacacaact catccccggc gtatccgtgc tggcctacct gccattcttc | 720 |
| cacgccttcg gcttcagtat caacctgggc tatttcatgg tgggcctgag agtggtgatg | 780 |
| ctccgaaggt ttaaccagga ggtgttcctg aaggccatcc aggactacga ggtgaggagc | 840 |
| gtgatcaacg ttccctccac aatcctgttc ctgtccaaga gccctctggt ggacaagtac | 900 |
| gacctatcca ccctggcgga gctgtgctgt ggagccgctc ctctggcgaa ggaggtggcc | 960 |
| gagatcgccg tgaagaggct gaacctgcca gggatacggt gtggctacgg tctaacagag | 1020 |
| tctacctccg ccaacatcca tactctgcac aacgagttca agtccggctc cctgggcaag | 1080 |
| gtgacacctt acatggccgc caagatcatc gacaggaaca ccggcgaggc cctgggtcca | 1140 |
| aaccaggtgg gcgagctgtg catctgggga cctatggtaa caaaaggcta tgtgaacaac | 1200 |

-continued

```
ccacaggcta ctaaggaggc catcgacgac gacggctggc tgcactctgg cgacttcggc    1260
tactacgacg aggacgagta tttctacatc gtggaccggt acaaggagct gatcaaatac    1320
aagggctatc aggtcgcccc tgtggagctg gaggagatcc tccttcagca cccaggcatc    1380
agggacgtgg ccgtcgtggg tatccctgac atcgaggccg gcgagctgcc agccggcttc    1440
gtggtgaagc agcccggcgc ccaactcacc gctaaggagg tgtacgactt cctggcccag    1500
agggtgtctc actccaagta cctgaggggc ggcgtaaggt tcgtggactc tatccccagg    1560
aacgtgacag gcaagattag tcgaaaagag ctgagggagg ccctgatgga gaaggcttct    1620
aagctgtaa                                                            1629
```

```
<210> SEQ ID NO 3
<211> LENGTH: 24
<212> TYPE: PRT
<213> ORGANISM: Simian virus 40

<400> SEQUENCE: 3

Asp Pro Lys Lys Lys Arg Lys Val Asp Pro Lys Lys Lys Arg Lys Val
1               5                   10                  15

Asp Pro Lys Lys Lys Arg Lys Val
            20

<210> SEQ ID NO 4
<211> LENGTH: 19
<212> TYPE: PRT
<213> ORGANISM: Mus musculus

<400> SEQUENCE: 4

Met Gly Trp Ser Cys Ile Ile Leu Phe Leu Val Ala Thr Ala Thr Gly
1               5                   10                  15

Ala His Ser

<210> SEQ ID NO 5
<211> LENGTH: 20
<212> TYPE: PRT
<213> ORGANISM: Mus musculus

<400> SEQUENCE: 5

Met Leu Cys Cys Met Arg Arg Thr Lys Gln Val Glu Lys Asn Asp Glu
1               5                   10                  15

Asp Gln Lys Ile
            20

<210> SEQ ID NO 6
<211> LENGTH: 6
<212> TYPE: PRT
<213> ORGANISM: Mus musculus

<400> SEQUENCE: 6

Ser Glu Lys Asp Glu Leu
1               5

<210> SEQ ID NO 7
<211> LENGTH: 123
<212> TYPE: DNA
<213> ORGANISM: Mus musculus

<400> SEQUENCE: 7
agccatggct tcccgccgga ggtggaggag caggatgatg gcacgctgcc catgtcttgt    60
gcccaggaga gcgggatgga ccgtcaccct gcagcctgtg cttctgctag gatcaatgtg    120
``` tag                                                                        123

<210> SEQ ID NO 8
<211> LENGTH: 40
<212> TYPE: PRT
<213> ORGANISM: Mus musculus

<400> SEQUENCE: 8

Ser His Gly Phe Pro Pro Glu Val Glu Glu Gln Asp Asp Gly Thr Leu
1               5                   10                  15

Pro Met Ser Cys Ala Gln Glu Ser Gly Met Asp Arg His Pro Ala Ala
            20                  25                  30

Cys Ala Ser Ala Arg Ile Asn Val
        35                  40

<210> SEQ ID NO 9
<211> LENGTH: 30
<212> TYPE: DNA
<213> ORGANISM: herpes simplex virus

<400> SEQUENCE: 9
gggactagtc tgcttcatcc ccgtggcccg                                            30

<210> SEQ ID NO 10
<211> LENGTH: 30
<212> TYPE: DNA
<213> ORGANISM: herpes simplex virus

<400> SEQUENCE: 10
gtggcctcga acaccgagcg accgatatcg                                            30

<210> SEQ ID NO 11
<211> LENGTH: 77
<212> TYPE: DNA
<213> ORGANISM: Artificial Sequence
<220> FEATURE:
<223> OTHER INFORMATION: Synthetic Sequence

<400> SEQUENCE: 11
tcgagcggaa agtcccacgg aaagtcccac ggaaagtccc acggaaagtc ccacggaaag          60
tcccacggaa agtccca                                                          77

<210> SEQ ID NO 12
<211> LENGTH: 77
<212> TYPE: DNA
<213> ORGANISM: Artificial Sequence
<220> FEATURE:
<223> OTHER INFORMATION: Synthetic Sequence

<400> SEQUENCE: 12
gatctgggac tttccgtggg actttccgtg gactttccg tggactttc cgtgggactt            60 tccgtgggac tttccgc                                                          77

<210> SEQ ID NO 13
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 13
tcgagatgag tcaaatgagt caaatgagtc aaatgagtca atgagtcaa atgagtcaa            59

```
<210> SEQ ID NO 14
<211> LENGTH: 59
<212> TYPE: DNA
<213> ORGANISM: Artificial Sequence
<220> FEATURE:
<223> OTHER INFORMATION: Synthetic Sequence

<400> SEQUENCE: 14
gatcttgact catttgactc atttgactca tttgactcat tgactcatt tgactcatc    59

<210> SEQ ID NO 15
<211> LENGTH: 8
<212> TYPE: PRT
<213> ORGANISM: Artificial Sequence
<220> FEATURE:
<223> OTHER INFORMATION: Synthetic Sequence

<400> SEQUENCE: 15

Met Asp Tyr Asp Asp Asp Asp Lys
1               5

<210> SEQ ID NO 16
<211> LENGTH: 24
<212> TYPE: PRT
<213> ORGANISM: Artificial Sequence
<220> FEATURE:
<223> OTHER INFORMATION: Synthetic Sequence

<400> SEQUENCE: 16

Asp Pro Lys Lys Lys Arg Lys Val Asp Pro Lys Lys Lys Arg Lys Val
1               5                   10                  15

Asp Pro Lys Lys Lys Arg Lys Val
            20

<210> SEQ ID NO 17
<211> LENGTH: 28
<212> TYPE: PRT
<213> ORGANISM: Artificial Sequence
<220> FEATURE:
<223> OTHER INFORMATION: Synthetic Sequence
<220> FEATURE:
<221> NAME/KEY: misc_feature
<222> LOCATION: (20)..(22)
<223> OTHER INFORMATION: Xaa can be any naturally occurring amino acid
      or no amino acid

<400> SEQUENCE: 17

Met Gly Trp Ser Cys Ile Ile Leu Phe Leu Val Ala Thr Ala Thr Gly
1               5                   10                  15

Ala His Ser Xaa Xaa Xaa Ser Glu Lys Asp Glu Leu
            20                  25

<210> SEQ ID NO 18
<211> LENGTH: 20
<212> TYPE: PRT
<213> ORGANISM: Artificial Sequence
<220> FEATURE:
<223> OTHER INFORMATION: Synthetic Sequence

<400> SEQUENCE: 18

Met Leu Cys Cys Met Arg Arg Thr Lys Gln Val Glu Lys Asn Asp Glu
1               5                   10                  15

Asp Gln Lys Ile
            20
```